United States Patent
Takahara et al.

(10) Patent No.: US 12,398,359 B2
(45) Date of Patent: Aug. 26, 2025

(54) CELL CULTURE DEVICE, CELL CULTURE METHOD, AND RECORDING MEDIUM

(71) Applicants: Mitsubishi Electric Corporation, Tokyo (JP); Keio University, Tokyo (JP)

(72) Inventors: Osamu Takahara, Tokyo (JP); Kazuhide Kodeki, Tokyo (JP); Akira Morikawa, Tokyo (JP); Tetsushi Azuma, Tokyo (JP); Kenjiro Takemura, Yokohama (JP); Yuta Kurashina, Yokohama (JP); Genichiro Fujii, Yokohama (JP)

(73) Assignees: MITSUBISHI ELECTRIC CORPORATION, Tokyo (JP); KEIO UNIVERSITY, Tokyo (JP)

( * ) Notice: Subject to any disclaimer, the term of this patent is extended or adjusted under 35 U.S.C. 154(b) by 1218 days.

(21) Appl. No.: 17/051,437

(22) PCT Filed: Jul. 5, 2018

(86) PCT No.: PCT/JP2018/025577
§ 371 (c)(1),
(2) Date: Oct. 29, 2020

(87) PCT Pub. No.: WO2020/008606
PCT Pub. Date: Jan. 9, 2020

(65) Prior Publication Data
US 2021/0054330 A1 Feb. 25, 2021

(51) Int. Cl.
*C12M 1/42* (2006.01)
*C12N 13/00* (2006.01)
*C12Q 3/00* (2006.01)

(52) U.S. Cl.
CPC ............. *C12M 35/04* (2013.01); *C12N 13/00* (2013.01); *C12Q 3/00* (2013.01)

(58) Field of Classification Search
None
See application file for complete search history.

(56) References Cited

U.S. PATENT DOCUMENTS 6,096,544 A * 8/2000 Bramble ................ C12M 27/16
435/395
9,952,122 B2 * 4/2018 Veiseh ................ G01N 21/253
(Continued)

FOREIGN PATENT DOCUMENTS

JP 63-13600 U 1/1988
JP 6-141850 A 5/1994
(Continued)

OTHER PUBLICATIONS

Zeiser, Arno, et al. "On-line monitoring of physiological parameters of insect cell cultures during the growth and infection process." Biotechnology progress 16.5 (2000): 803-808. (Year: 2000).*
(Continued)

*Primary Examiner* — William H. Beisner
(74) *Attorney, Agent, or Firm* — XSENSUS LLP

(57) ABSTRACT

An ultrasonic transducer (10) emits ultrasonic waves toward a culture solution (3) stored with cells (2) in a culture vessel (1). An acquirer acquires information indicating a settling state of the cells (2) in the culture solution (3). A controller controls an operation of the ultrasonic transducer (10) based on the information indicating the settling state of the cells (2).

12 Claims, 21 Drawing Sheets

(56) References Cited

U.S. PATENT DOCUMENTS

2004/0241832 A1    12/2004    Muraki et al.
2017/0191022 A1*    7/2017    Lipkens ................ C12M 29/02

FOREIGN PATENT DOCUMENTS

| JP | 10-113167 A | 5/1998 |
| JP | 2004-357523 A | 12/2004 |
| JP | 2009-156792 A | 7/2009 |
| JP | 2010-169579 A | 8/2010 |
| WO | 2017/056695 A1 | 4/2017 |

OTHER PUBLICATIONS

Zerai et al., Flow Characterization Through a Network Cell Using Particle Image Velocimetry., 2005, Transp Porous Med 60, 159-181 (Year: 2005).*
Al-Rubeai et al., Death Mechanisms of Animal Cells in Conditions of Intensive Agitation, 1995, Biotechnology and Bioengineering, 45, 463-538 (Year: 1995).*
Chinese Office Action issued May 22, 2023 in corresponding Chinese Patent Application No. 201880093589.0 (with English translation), 19 pages.
International Search Report and Written Opinion mailed on Sep. 25, 2018 for PCT/JP2018/025577 filed on Jul. 5, 2018, 8 pages including English Translation of the International Search Report.
Kurashina et al., "Cell agglomeration in the wells of a 24-well plate using acoustic streaming", The Royal Society of Chemistry, Feb. 10, 2017, 11 pages.

* cited by examiner

CELL CULTURE DEVICE, CELL CULTURE METHOD, AND RECORDING MEDIUM

CROSS-REFERENCE TO RELATED APPLICATION

The present application is based on PCT filing PCT/JP2018/025577, filed Jul. 5, 2018, the entire contents of which are incorporated herein by reference.

TECHNICAL FIELD

The present disclosure relates to a cell culture device, a cell culture method, and a cell culture program.

BACKGROUND ART

Suspension culture techniques have been developed for culturing animal cells for use in regenerative medicine. For example, Patent Literature 1 describes a cell culture device that irradiates cell aggregates in a culture solution with ultrasonic waves to break up the cell aggregates while stirring the solution with a stirring blade. The cell culture device stirs the culture solution to reduce uneven distributions of nutrient components and dissolved oxygen in the culture solution and to reduce gathering of cells resulting from cell settling.

The cell culture device described in Patent Literature 1 may damage cells with the stirring blade for stirring the culture solution. To avoid such damage to cells with a stirring blade, a culture device described in Patent Literature 2 uses ultrasonic irradiation to stir a cell suspension.

CITATION LIST

Patent Literature

Patent Literature 1: International Publication No. WO 2017/056695
Patent Literature 2: Unexamined Japanese Utility Model Application Publication No. 63-013600

SUMMARY OF INVENTION

Technical Problem

The culture device described in Patent Literature 2 constantly performs ultrasonic irradiation for stirring a cell suspension. However, constant ultrasonic irradiation may affect cells in the cell suspension and raise the temperature of the culture solution, thus adversely affecting the cells.

In response to the above issue, an objective of the present disclosure is to culture cells efficiently without excessive ultrasonic irradiation to a culture solution in stirring the solution using ultrasonic waves.

Solution to Problem

To achieve the above objective, a cell culture device according to an aspect of the present disclosure includes an irradiator, an acquirer, and a controller. The irradiator emits ultrasonic waves toward a culture solution stored with cells in a culture vessel. The acquirer acquires information indicating a settling state of the cells in the culture solution. The controller controls an operation of the irradiator based on the information indicating the settling state of the cells.

Advantageous Effects of Invention

The technique according to the above aspect of the present disclosure allows ultrasonic irradiation to a culture solution in accordance with the settling state of cells in the culture solution. The culture solution with settling cells is thus stirred using ultrasonic waves, and the culture solution with sufficiently suspended cells is not irradiated with ultrasonic waves. The technique thus enables efficient culture of cells without excessive ultrasonic irradiation to a culture solution in stirring the solution using ultrasonic waves.

DESCRIPTION OF EMBODIMENTS

Figure 1:
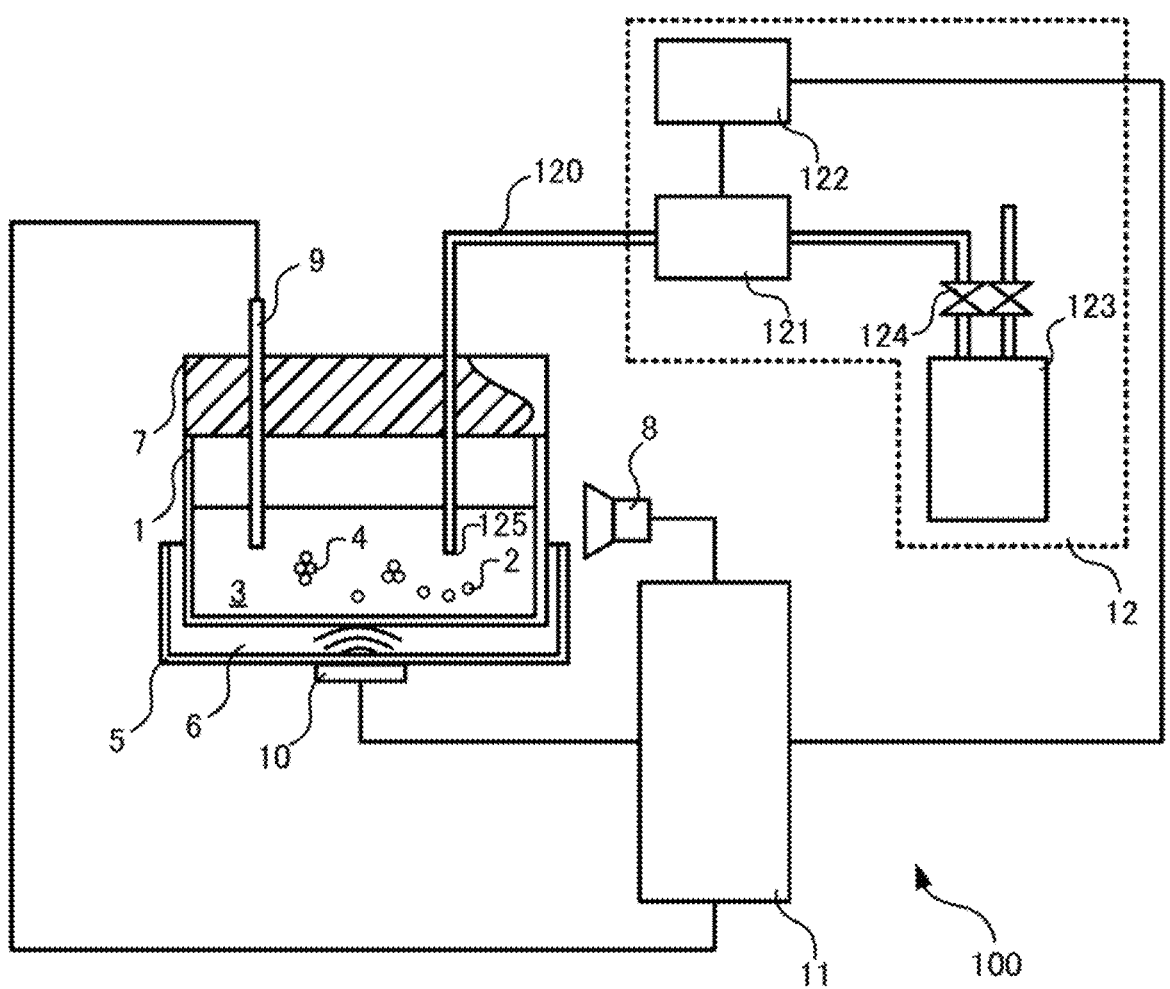
FIG. 1 is a schematic diagram of a cell culture device according to Embodiment 1 of the present disclosure.

A cell culture device according to embodiments of the present disclosure will now be described in detail with reference to the drawings. Throughout the drawings, the same or equivalent components are denoted by the same reference numerals.

Embodiment 1

FIG. 1 is a schematic diagram of a cell culture device 100 according to Embodiment 1 of the present disclosure. The cell culture device 100 cultures cells 2 stored in a culture vessel 1. When culturing cells 2, the cell culture device 100 stirs a culture solution 3 stored with the cells 2 in the culture vessel 1. The culture vessel 1 is a cylinder with a circular bottom surface and an upper opening. The culture vessel 1 is formed from poly carbonate.

The cells 2 are animal cells culturable in suspension. Multiple cells 2 resulting from cell division may form a cell aggregate 4. The culture solution 3 has a composition suitable for culturing cells 2. The culture solution 3 contains, in addition to a liquid culture medium, for example, an organic substance, a pH buffer solution, a blood serum, minerals, an antibiotic, and a pH indicator. The cells 2 described below include cell aggregates 4.

Figure 2:
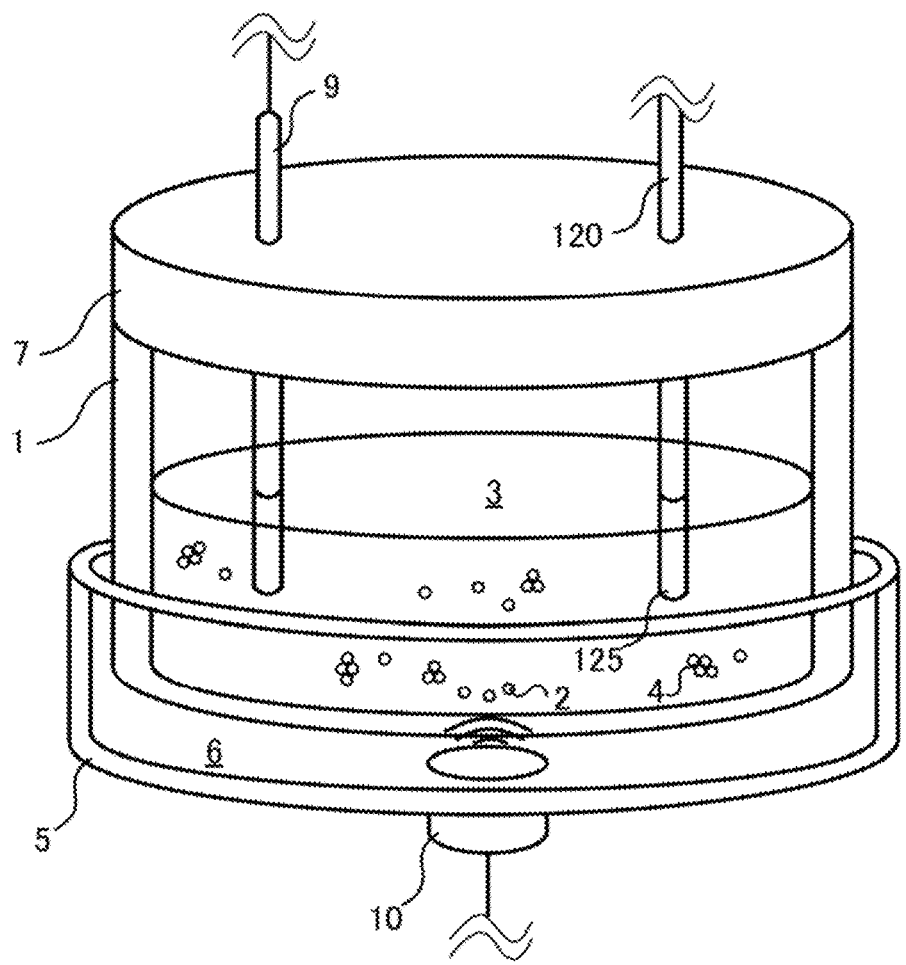
FIG. 2 is a partial perspective view of the cell culture device shown in FIG. 1.

As shown in FIG. 2, the culture vessel 1 is placed inside a tank 5 having an upper opening. The tank 5 is filled with a liquid 6. The liquid 6 is water or oil. The upper opening of the culture vessel 1 is covered with a lid 7.

The cell culture device 100 includes an optical sensor 8 that captures an image of the culture solution 3, a culture solution sensor 9 that measures the oxygen concentration, an ultrasonic transducer 10 that emits ultrasonic waves, a control unit 11, and a cell collection unit 12 that collects cells 2. The control unit 11 controls the operation of the optical sensor 8, the culture solution sensor 9, the ultrasonic transducer 10, and the cell collection unit 12. An ultrasonic transducer is hereafter simply referred to as a transducer.

The optical sensor 8 is connected to the control unit 11. The optical sensor 8 captures an image of the culture solution 3 containing the cells 2 stored in the culture vessel 1. Image data corresponding to an image captured by the optical sensor 8 is transmitted to the control unit 11.

The culture solution sensor 9 extends through the lid 7 and is immersed in the culture solution 3. The culture solution sensor 9 measures the concentration of oxygen dissolved in the culture solution 3. The culture solution sensor 9 is connected to the control unit 11. Information indicating the oxygen concentration measured by the culture solution sensor 9 is transmitted to the control unit 11.

The transducer 10 is embedded in a viscoelastic member attached on the bottom surface of the tank 5 to be fixed to the tank 5. The transducer 10 includes a piezoelectric element. Upon receiving a driving voltage, the piezoelectric element vibrates toward the central axis of the transducer 10, causing the transducer 10 to emit ultrasonic waves (compression waves). The emitted ultrasonic waves propagate along the central axis. The ultrasonic waves emitted from the transducer 10 have the central axis perpendicular to the bottom surface of the tank 5. The transducer 10 functions as an irradiator to emit ultrasonic waves toward the culture solution 3. The ultrasonic waves herein are elastic vibration waves having a frequency of 20 kHz or more.

Figure 3:
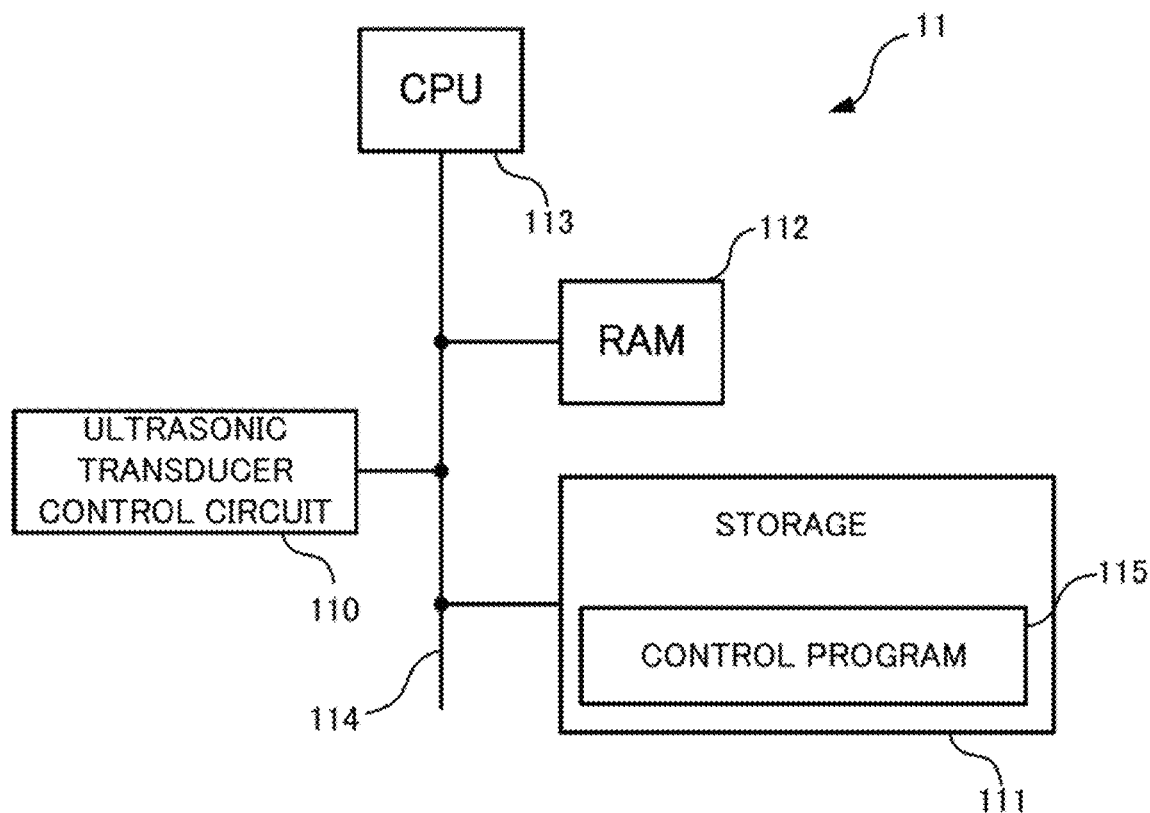
FIG. 3 is a block diagram of a control unit shown in FIG. 1 showing the hardware configuration.

The transducer 10 is connected to the control unit 11. As shown in FIG. 3, the control unit 11 includes an ultrasonic transducer control circuit 110, a storage 111, a random-access memory (RAM) 112, a central processing unit (CPU) 113, and a bus 114. The ultrasonic transducer control circuit 110, the storage 111, the RAM 112, and the CPU 113 are connected to one another with the bus 114.

The ultrasonic transducer control circuit 110 generates a driving voltage corresponding to the frequency and amplitude of the ultrasonic waves to be emitted from the transducer 10. The control unit 11 applies the driving voltage generated by the ultrasonic transducer control circuit 110 to the transducer 10. The transducer 10 vibrates in accordance with the driving voltage. To reduce either death or decrease in the number of cells 2, the control unit 11 controls the amplitude of the driving voltage to have a sound pressure of 300 kPa or less in the culture vessel 1 resulting from the ultrasonic waves.

Figure 4:
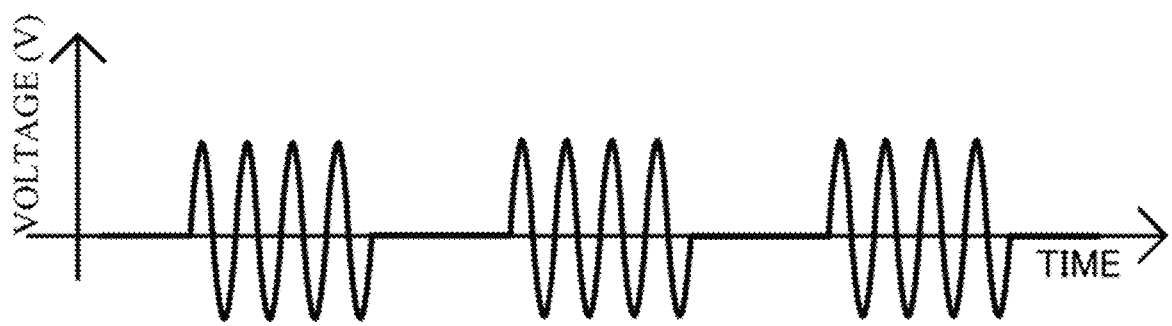
FIG. 4 is a diagram showing the waveform of a driving voltage applied to an ultrasonic transducer in the cell culture device shown in FIG. 1.

As shown in FIG. 4, the control unit 11 intermittently applies the driving voltage to the transducer 10. This drives and stops the transducer 10 in a repeated manner at regular intervals. In more detail, the control unit 11 drives the transducer 10 for 30 seconds and then stops the transducer 10 for 90 seconds. The ultrasonic waves have a frequency of 158 kHz.

The storage 111 includes a non-volatile storage medium such as a read-only memory (ROM), a hard disk drive (HDD), and a flash memory, and stores a control program 115 and various sets of data.

The RAM 112 functions as a main memory for the CPU 113. When the CPU 113 executes the control program 115, the control program 115 is loaded in the RAM 112.

The CPU 113 reads, in addition to the control program 115, various software programs stored in the storage 111 into the RAM 112 and executes the software programs. This allows the control unit 11 to cause the optical sensor 8, the culture solution sensor 9, the transducer 10, and the cell collection unit 12 to perform the operations below.

Figure 5:
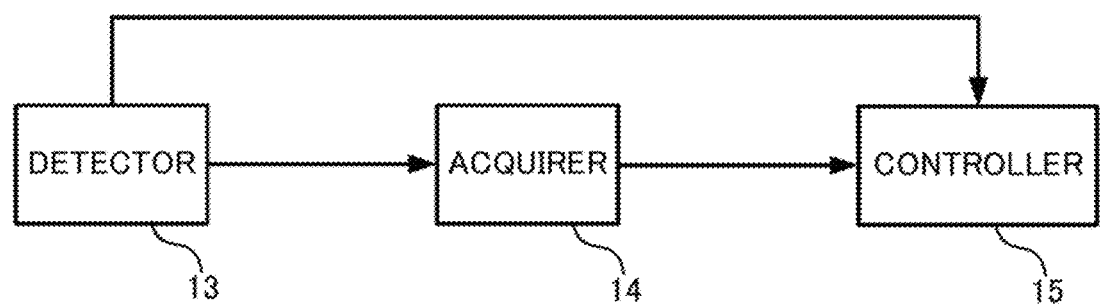
FIG. 5 is a functional block diagram of a central processing unit (CPU) included in the control unit shown in FIG. 1.

FIG. 5 is a functional block diagram of the CPU 113. The control program 115 causes the CPU 113 to function as a detector 13 that detects cells 2 in the culture solution 3, an acquirer 14 that acquires information indicating the settling state of cells 2 in the culture solution 3, and a controller 15 that controls the operation of the transducer 10 based on the information indicating the settling state of cells 2.

The detector 13 uses edge detection to recognize an image captured by the optical sensor 8. The detector 13 extracts the boundary between a cell 2 and the culture solution 3 in the image. For a shape with an edge defined by a boundary having a predetermined degree of similarity to a shape prestored in the storage 111 to be a shape of a cell 2, the detector 13 detects the shape with the edge defined by the boundary to be the shape of a cell 2.

The detector 13 associates image data and information about the boundary between the cell 2 and the culture solution 3 in the image corresponding to the image data with the time at which the image is captured, and stores the data and the information into the storage 111.

The detector 13 detects the concentration of oxygen contained in the culture solution 3 with the culture solution sensor 9. The detector 13 outputs information indicating the oxygen concentration to the controller 15.

The acquirer 14 acquires positional information about cells 2 in the culture vessel 1 included in the image captured by the optical sensor 8. When acquiring the positional information, the acquirer 14 sets, on an image corresponding to the image data stored in the storage 111, coordinate axes corresponding to a height direction from the bottom surface of the culture vessel 1 and to a horizontal direction. The acquirer 14 acquires the coordinates of the cell 2 on a coordinate plane in the image as positional information. The positional information about the cell 2 is, for example, a range of coordinates for an edge of the shape detected as the cell 2 on the coordinate plane.

The acquirer 14 associates image data with the positional information about the cell 2 included in the image corresponding to the image data, and stores the positional information into the storage 111. When multiple cells 2 are included in the image corresponding to the image data, the acquirer 14 assigns an identification number to each cell 2 and stores positional information associated with each identification number into the storage 111.

Figure 6:
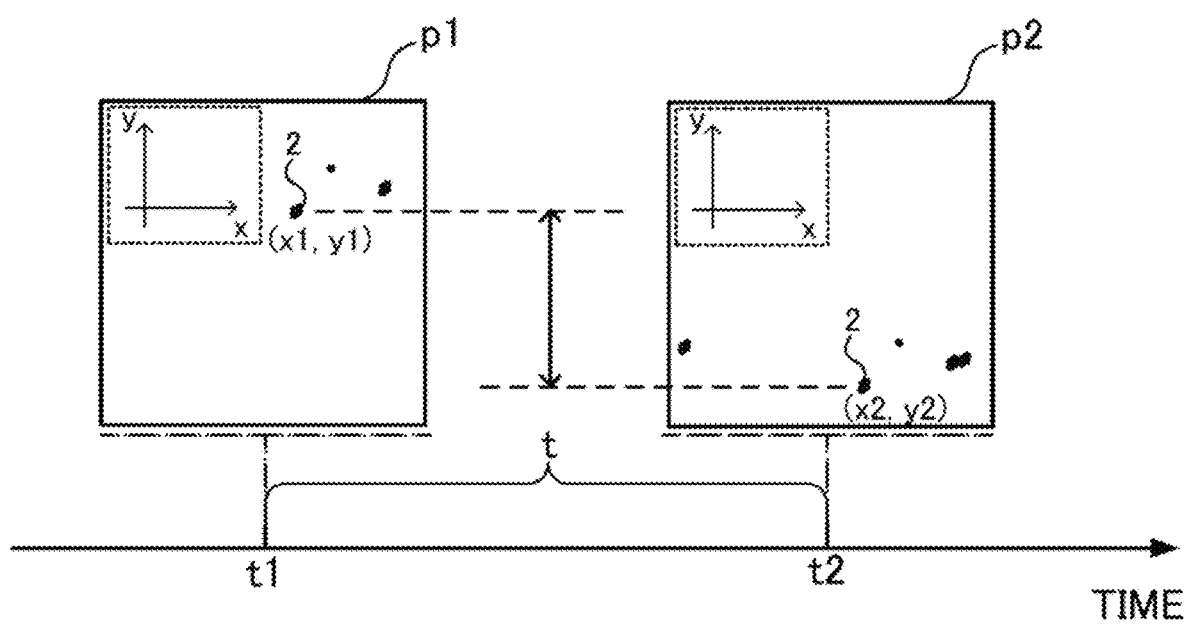
FIG. 6 is a conceptual diagram of calculating the settling velocity by image analysis.

The acquirer 14 calculates, as information indicating the settling state of cells 2, a settling distance per unit time for a cell 2 detected by the detector 13, or in other words, a settling velocity. Calculation of the settling velocity will now be described with reference to FIG. 6. The acquirer 14 refers to image data corresponding to an image p1 captured at a time t1 and stored in the storage 111 and image data corresponding to an image p2 captured at a time t2 and stored in the storage 111. The acquirer 14 sets, for each of the image p1 and the image p2, the x-axis with reference to the center of the horizontal cross section of the culture vessel 1 and the y-axis extending in the height direction with respect to the bottom surface of the culture vessel 1. The x- and y-axes set in the images p1 and p2 have the same scale.

The acquirer 14 calculates a distance traveled by a cell 2 toward the bottom surface as a settling distance based on positional information about the cell 2 included in the image p1, or more specifically, the coordinates (x1, y1), and the coordinates (x2, y2) of the cell 2 included in the image p2. The acquirer 14 then calculates the settling velocity of the cell 2 by dividing the settling distance by the elapsed time t determined by subtracting t1 from t2. The acquirer 14 outputs information indicating the calculated settling velocity to the controller 15.

The acquirer 14 measures the size of a cell 2 detected by the detector 13. In detail, the acquirer 14 refers to image data stored in the storage 111, and measures the size of the cell 2 based on the image magnification and the diameter or area of the cell 2 in the image. The acquirer 14 outputs information indicating the acquired size of the cell 2 to the controller 15.

The controller 15 controls the operation of the transducer 10 based on the information indicating the settling state of cells 2. The controller 15 compares the settling velocity of a cell 2 as the information indicating the settling state of the cell 2 with a threshold $N_v$ prestored in the storage 111. Cells 2 settling at a velocity higher than or equal to $N_v$ may continue settling. Without being suspended, the cells 2 may gather at the bottom surface of the culture vessel 1. Such cells 2 are difficult to grow. When cells 2 settle at a velocity higher than or equal to $N_v$, the controller 15 applies a driving voltage to the transducer 10.

When the controller 15 applies a driving voltage to the transducer 10, ultrasonic waves are emitted toward the culture solution 3. In more detail, acoustic radiation pressure produced by the vibrating transducer 10 propagates in the liquid 6 adjacent to an end surface of the transducer 10. The acoustic radiation pressure further propagates through the bottom surface of the culture vessel 1 to reach the culture solution 3. The acoustic radiation pressure produces acoustic streaming in the culture solution 3. The acoustic streaming reduces settling of cells 2 in the culture vessel 1 or suspends the cells 2, thus preventing the cells 2 from gathering at the bottom surface of the culture vessel 1.

The controller 15 controls the operation of the transducer 10 based on the information indicating the size of a cell 2. A larger cell 2 tends to settle at a higher velocity. Thus, ultrasonic irradiation for a longer duration for larger cells 2 can effectively reduce settling of the cells 2. The controller 15 increases the duration for ultrasonic irradiation by the transducer 10 in accordance with the size of a cell 2. In more detail, the storage 111 stores a table associating a size range of a cell 2 with a duration for ultrasonic irradiation. In the table, a cell 2 with a larger size is associated with a proportionally longer irradiation duration. The controller 15 refers to the table and emits ultrasonic waves with the transducer 10 for an irradiation duration in accordance with the size of a cell 2 acquired by the acquirer 14.

The controller 15 controls the operation of the irradiator based on information indicating the oxygen concentration. More specifically, the controller 15 compares the oxygen concentration detected by the detector 13 with a threshold $N_{oxy}$ prestored in the storage 111. When the oxygen concentration is lower than or equal to $N_{oxy}$, oxygen may be insufficient, thus decreasing the growth efficiency of cells 2. When the oxygen concentration is lower than or equal to $N_{oxy}$, the controller 15 emits ultrasonic waves with the transducer 10. Acoustic streaming produced in the culture solution 3 by the ultrasonic irradiation stirs the culture solution 3. This facilitates taking oxygen from the atmosphere into the culture solution 3. When insufficient oxygen is taken into the culture solution 3 by stirring the culture solution 3, oxygen may be provided to the culture solution 3 by forced aeration performed with a diffuser tube immersed in the culture solution 3.

The controller 15 controls, in addition to the transducer 10, the optical sensor 8, the culture solution sensor 9, and the cell collection unit 12.

The cell collection unit 12 includes a tube 120, a suction pump 121, a suction pump controller 122, a collection bag 123, and an open-close valve 124. The cell collection unit 12 is connected to the control unit 11 through the suction pump controller 122. The controller 15 functions as a collector to collect cells 2 with the cell collection unit 12.

The tube 120 has both ends open, with one end serving as an inlet port 125. The tube 120 extends through the lid 7 with the inlet port 125 immersed in the culture solution 3. The tube 120 has the other end connected to the suction pump 121. The suction pump 121 is connected to the suction pump controller 122.

The suction pump controller 122 includes a CPU, an external storage device, and a RAM (not shown). As controlled by the controller 15, the CPU reads a software program stored in the external storage device into the RAM and controls the execution of the software program to allow the suction pump controller 122 to control the operation of the suction pump 121.

The collection bag 123 is connected to the suction pump 121 through the open-close valve 124. When the open-close valve 124 is closed, air is prevented from flowing into the collection bag 123 through the suction pump 121. When the open-close valve 124 is open, air can flow into the collection bag 123 through the suction pump 121.

When the suction pump controller 122 drives the suction pump 121 with the open-close valve 124 being open, the suction pump 121 performs suction through the inlet port 125. The inlet port 125 immersed in the culture solution 3 sucks cells 2 together with the culture solution 3 contained in the culture vessel 1. The sucked culture solution 3 and cells 2 are fed to the collection bag 123. In this manner, the cell culture device 100 collects cells 2.

To collect cells 2, the acquirer 14 acquires information indicating a change in the number of cells 2 in the culture solution 3 detected by the detector 13. More specifically, the acquirer 14 counts the number of cells 2 included in the image p1 and the number of cells 2 included in the image p2. The acquirer 14 then calculates the rate of change in the number of cells 2 at the elapsed time t based on the number of cells 2 included in each of the images p1 and p2. The acquirer 14 outputs, to the controller 15, information indicating the rate of change in the number of cells 2 as information indicating the change in the number of cells 2.

The controller 15 collects cells 2 based on the information indicating the change in the number of cells 2. In this example, the controller 15 compares the rate of change with a threshold $N_r$ prestored in the storage 111. When the rate of change is lower than or equal to Nr, the number of cells 2 changes by a small amount and the growth of cells 2 in the culture solution 3 is in a stationary phase. Cells 2 do not increase greatly in a stationary phase. The controller 15 thus transmits, to the suction pump controller 122, instruction data to instruct collection of cells 2.

When receiving the instruction data from the controller 15, the suction pump controller 122 collects cells 2. When a predetermined volume of culture solution 3 is collected in the collection bag 123, the suction pump controller 122 stops suction with the suction pump 121. The open-close valve 124 is closed to acquire the collection bag 123 storing the cells 2.

The use and operation of the cell culture device 100 according to the present embodiment will now be described. The cell culture device 100 is installed under an atmosphere of air of 37° C. with the concentration of carbon dioxide kept at 5%. The cell culture device 100 is installed in an enclosed space to avoid external contamination of the culture solution 3.

After being installed, the cell culture device 100 is left until the culture solution 3 stored in the culture vessel 1 placed in the tank 5 stabilizes under the atmosphere. Subsequently, at least $10^7$ cells 2 are seeded in the culture solution 3 with a sterilized pipette.

Figure 7:
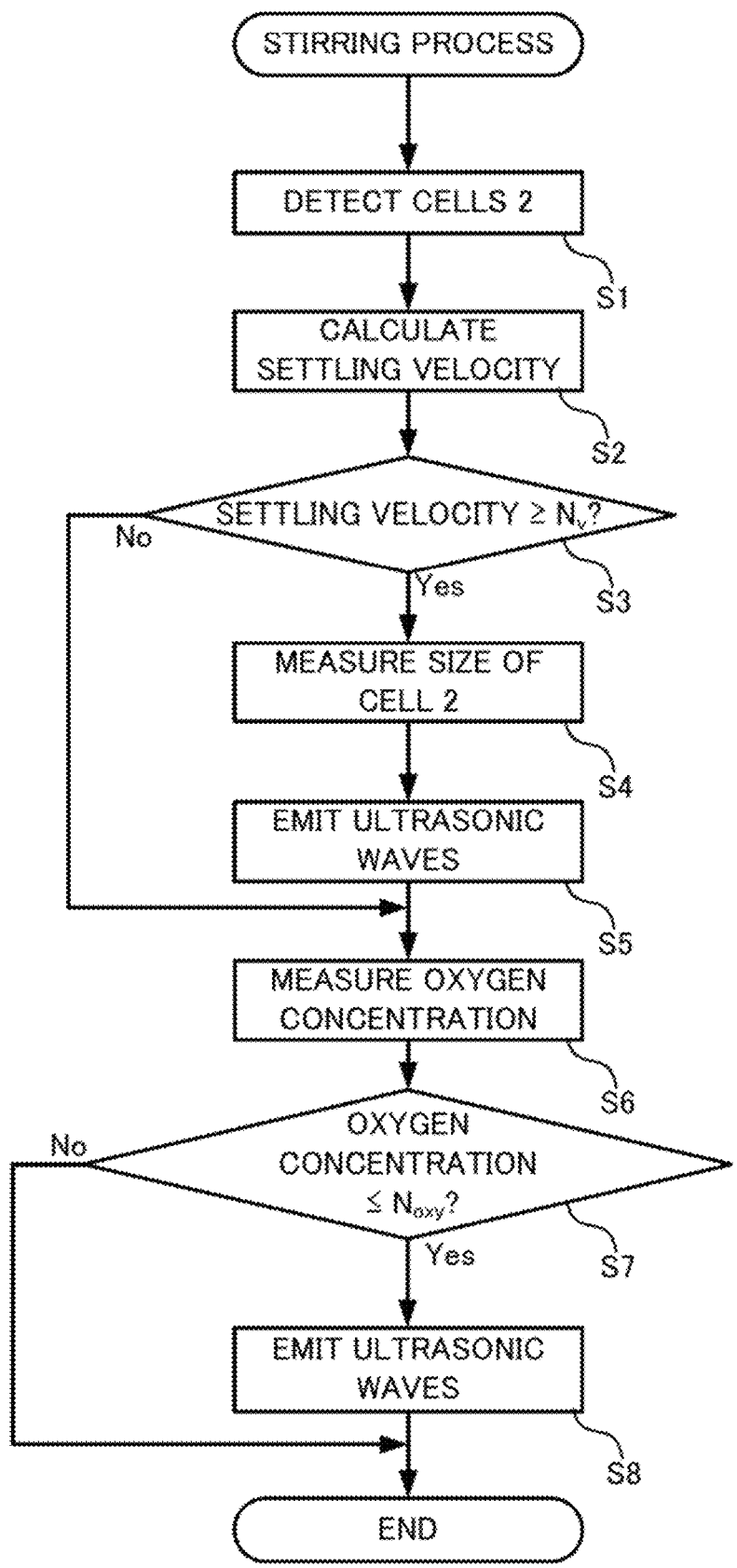
FIG. 7 is a flowchart of a stirring process performed by the cell culture device shown in FIG. 1.

FIG. 7 is a flowchart of a stirring process performed by the cell culture device 100. When a predetermined time period has elapsed after the start of culturing, the detector 13 detects cells 2 in the culture solution 3 (step S1). The acquirer 14 calculates a settling velocity based on positional information (step S2). The controller 15 determines whether the settling velocity of a cell 2 is higher than or equal to $N_v$ (step S3). When the settling velocity is lower than $N_v$ (No in step S3), the controller 15 advances to step S6.

When the settling velocity is higher than or equal to $N_v$ (Yes in step S3), the acquirer 14 measures the size of a cell 2 (step S4). The controller 15 emits, with the transducer 10, ultrasonic waves toward the culture solution 3 for an irradiation duration in accordance with the size of a cell 2 (step S5).

The controller 15 then measures the concentration of oxygen dissolved in the culture solution 3 with the culture solution sensor 9 (step S6). The controller 15 determines whether the oxygen concentration is lower than or equal to the threshold $N_{oxy}$ (step S7). When the oxygen concentration is lower than or equal to $N_{oxy}$ (Yes in step S7), the controller 15 emits, with the transducer 10, ultrasonic waves toward the culture solution 3 (step S8). When the oxygen concentration is higher than $N_{oxy}$ (No in step S7), the controller 15 ends the stirring process.

Figure 8:
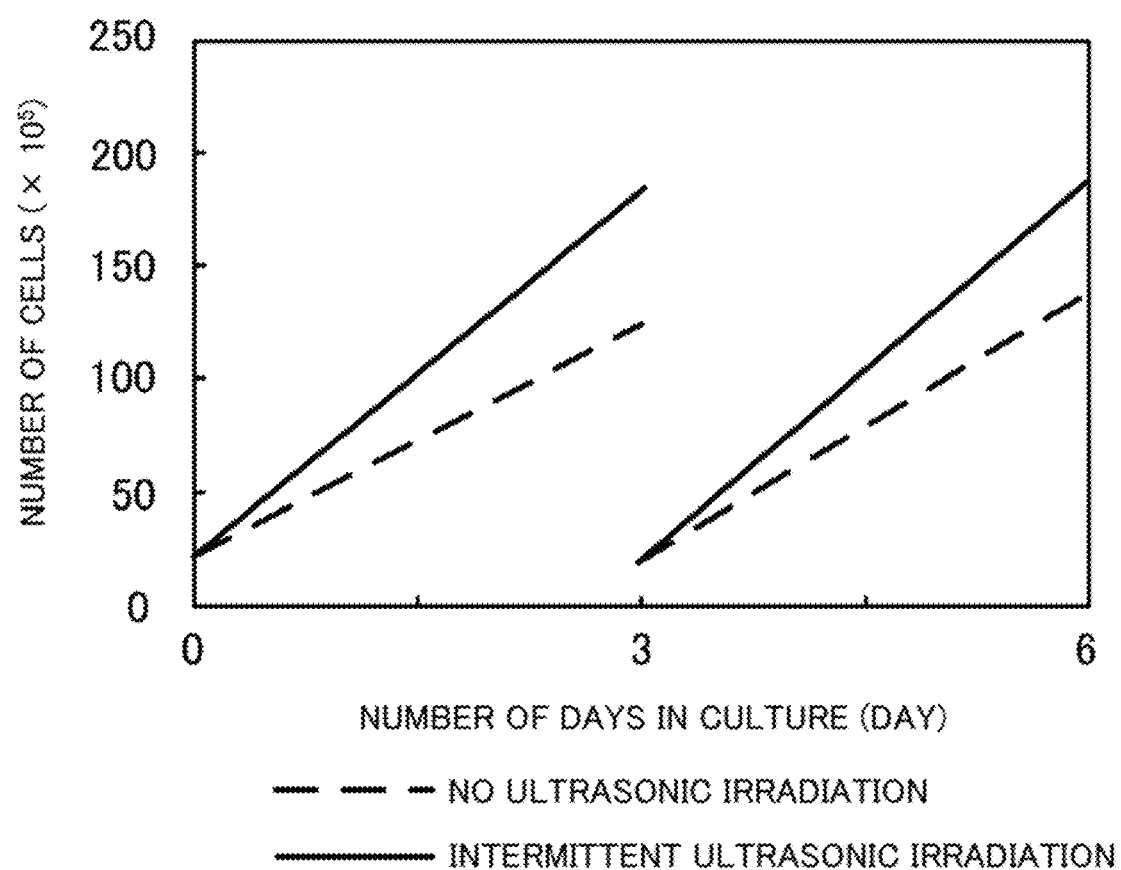
FIG. 8 is a graph showing the number of cells cultured in the cell culture device shown in FIG. 1 with respect to the culture time under intermittent ultrasonic irradiation from the start of culturing and under no ultrasonic irradiation.

FIG. 8 shows temporal changes in the number of cells 2 cultured in the cell culture device 100 under intermittent ultrasonic irradiation from the start of culturing and under no ultrasonic irradiation. Cells 2 are seeded in the culture solution 3 on day 0 and collected on day 3. After collection, cells 2 are seeded in a replaced culture solution 3 and then collected on day 6. The growth efficiency of the cells 2 is higher when the cells 2 are cultured under intermittent ultrasonic irradiation with the cell culture device 100 than when the cells 2 are cultured under no ultrasonic irradiation.

Figure 9:
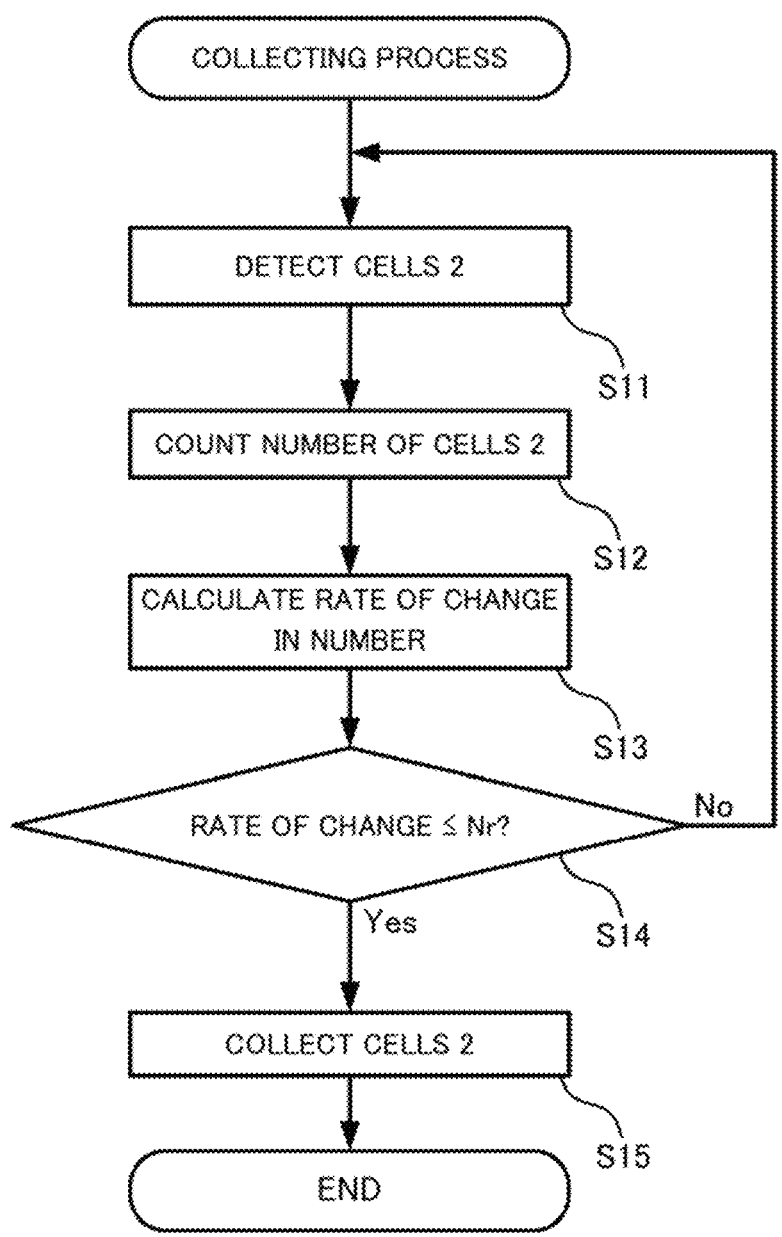
FIG. 9 is a flowchart of a collecting process performed by the cell culture device shown in FIG. 1.

A process of collecting cells 2 with the cell culture device 100 will now be described with reference to FIG. 9. The detector 13 first detects cells 2 in the culture solution 3 (step S11). The acquirer 14 counts the number of cells 2 included in the image p1 and the number of cells 2 included in the image p2 (step S12).

The acquirer 14 then calculates the rate of change in the number of cells 2 (step S13). The controller 15 determines whether the rate of change in the number of cells 2 is lower than or equal to $N_r$ (step S14). When the rate of change in the number of cells 2 is lower than or equal to $N_r$ (Yes in step S14), the controller 15 provides an instruction to collect cells 2 (step S15) and ends the collecting process. In this manner, the cells 2 are collected in the collection bag 123. When the rate of change in the number of cells 2 is higher than $N_r$ (No in step S14), the controller 15 returns to step S11.

As described above, the cell culture device 100 according to Embodiment 1 allows ultrasonic irradiation to the culture solution 3 in accordance with the settling state of cells 2 in the culture solution 3. The culture solution 3 with settling cells 2 is thus stirred, and the culture solution 3 with sufficiently suspended cells 2 is not stirred. In culturing cells 2, stirring may be performed to a degree sufficient to reduce settling of cells 2, rather than being performed constantly. This can prevent excessive ultrasonic irradiation to the culture solution 3.

The cell culture device 100 allows ultrasonic irradiation to the culture solution 3 in accordance with the settling state of cells 2 in the culture solution 3. This can reduce temperature increase in the liquid 6 and the culture solution 3 that may result from constant ultrasonic irradiation, and maintain the temperature of the culture solution 3 suitable for culturing cells 2, or specifically, at around 37° C. This structure reduces decreases in the growth rate and survival rate of cells 2 without providing excessive stress to the cells 2.

The cell culture device 100 collects cells 2 in accordance with the rate of change in the number of cells 2 at an elapsed time t. The cell culture device 100 thus continues culturing cells 2 growing insufficiently in an exponential growth phase, and collects cells 2 that have sufficiently grown in a stationary phase, thus enabling efficient culturing of cells 2. The elapsed time t may be set in any manner based on the growth rate and the characteristics of the cells 2.

The cell culture device 100 uses, in place of a stirring blade, ultrasonic waves to stir the culture solution 3. This structure can reduce contamination caused by repeated use of the same stirring blade.

In the present embodiment, the culture vessel 1 may be formed from any plastic material other than polycarbonate that is sterilizable in an autoclave, or glass. The culture vessel 1 may be formed from, for example, polystyrene.

Figure 10:
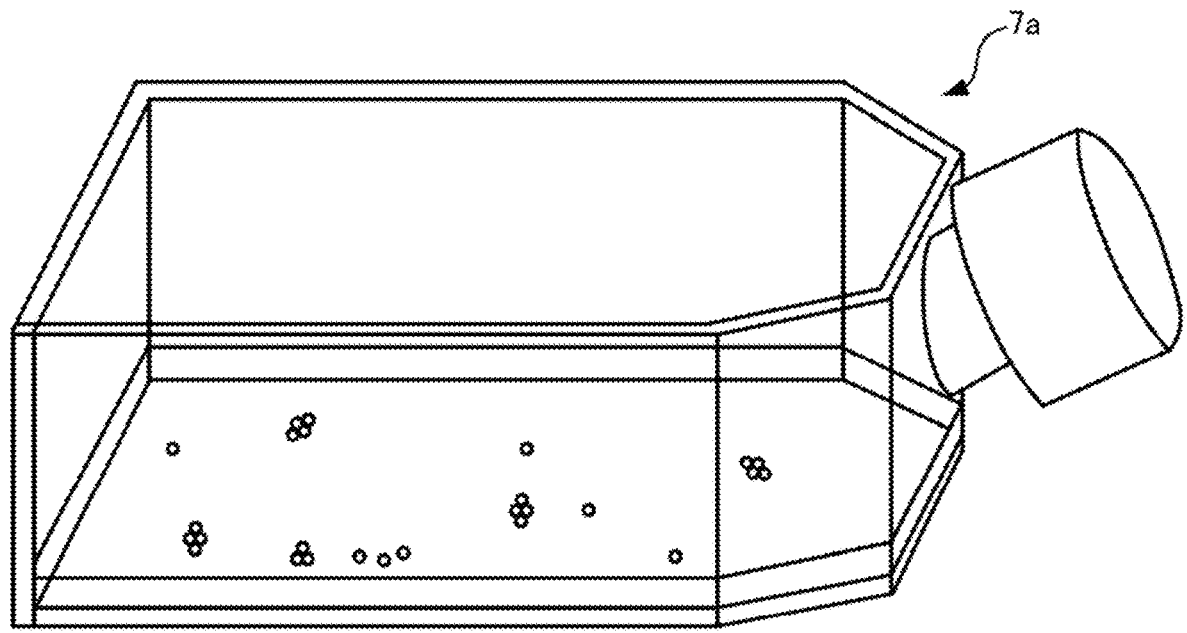
FIG. 10 is a perspective view of a cell culture flask as an example of a culture vessel.

The culture vessel 1 used in the present embodiment is a cylinder with a circular bottom surface, but may have any shape. The culture vessel 1 may for example be a cell culture flask 7a shown in FIG. 10. The shape of the tank 5 may be modified in accordance with the shape of the culture vessel 1.

The liquid 6 is water or oil. The liquid 6 may be replaced with any substance having acoustic impedance close to the acoustic impedance of the culture vessel 1. For example, such substances have the same acoustic impedance as water.

Although at least $10^7$ cells 2 are seeded in the culture solution 3 in the present embodiment, the number of cells 2 to seed may be adjusted as appropriate in accordance with the capacity of the culture vessel 1 and the growth rate of the cells 2.

The optical sensor 8 may cover ultraviolet to infrared regions, and may have any sensitive wavelength region. Although the optical sensor 8 is desirably a sensor that captures an image such as a charge-coupled device (CCD) camera, the optical sensor 8 may not be a sensor that captures an image. The cell culture device 100 may include, in place of the optical sensor 8, a spectrophotometer used with a turbidity method to measure the concentration of cells 2. With a spectrophotometer, the absorbance in a wavelength suitable for measuring the concentration of cells 2 is measured near the bottom surface of the culture vessel 1 and near the liquid level of the culture solution 3. In this case, for example, the ratio of the concentration D2 of cells 2 calculated based on the absorbance near the bottom surface to the concentration D1 of cells 2 calculated based on the absorbance near the liquid level, or specifically, D2/D1, may be used as information indicating the settling state of cells 2 in the culture solution 3. When the ratio D2/D1 is greater than a threshold, the controller 15 may emit ultrasonic waves toward the culture solution 3.

The settling velocity of a cell 2 may be calculated by measuring the settling distance of the cell 2 in the image captured by the optical sensor 8 in real time.

The optical sensor 8 may constantly or intermittently capture images. The optical sensor 8 may sequentially or intermittently transmit image data to the CPU 113. The acquirer 14 can acquire information indicating the settling state of cells 2 in the culture solution 3 from any piece of image data stored in the storage 111. In the present embodiment, the stirring process starts when a predetermined time period has elapsed after the start of culturing. The predetermined time period is determined in accordance with the number, growth rate, and characteristics of the cells 2 seeded. The stirring process may start in response to an instruction from a user.

In the stirring process described above, the controller 15 advances to step S6 when the settling velocity is lower than $N_v$ (No in step S3). The controller 15 may instead return to step S1.

The collecting process may start at any specified time. For example, the controller 15 may start the collecting process immediately after the culture solution 3 is stirred by ultrasonic irradiation in the stirring process. This allows capturing an image of cells 2 dispersed in the stirred culture solution 3, thus enabling more accurate detection of cells 2 with the detector 13. In the collecting process, the controller 15 returns to step S11 when the rate of change in the number of cells 2 is higher than $N_r$ (No in step S14). The controller 15 may instead end the collecting process.

Although the cell culture device 100 is installed in an enclosed space in the present embodiment, the cell culture device 100 may not be installed in an enclosed space when a temperature control device is installed in the culture vessel 1 and the concentration of carbon dioxide is adjusted in the culture vessel 1.

Although the ultrasonic waves emitted from the transducer 10 have the central axis perpendicular to the bottom surface of the tank 5 in the present embodiment, the central axis may not be perpendicular to the bottom surface of the tank 5. When the transducer 10 is installed, the central axis of the ultrasonic waves may be inclined at any angle with respect to the bottom surface of the tank 5. The central axis of the ultrasonic waves emitted from the transducer 10 may not be parallel to the bottom surface of the tank 5 to allow ultrasonic irradiation to reduce settling of cells 2. Although the ultrasonic waves have a frequency of 158 kHz in the present embodiment, any frequency may be used in accordance with the characteristics of the transducer 10 used.

Although intermittent irradiation involves driving the transducer 10 with the controller 15 for 30 seconds and stopping the transducer 10 for 90 seconds in the present embodiment, such intermittent irradiation may be performed under any other conditions. Another condition for intermittent irradiation includes, for example, a single ultrasonic irradiation operation followed by no ultrasonic irradiation for a duration nine times longer than the irradiation duration.

The controller 15 may flexibly control the transducer 10 in accordance with the settling velocity of a cell 2 by appropriately adjusting the driving voltage, the driving time, and the frequency of driving voltage applied to the transducer 10, instead of adjusting the irradiation duration.

In the present embodiment, ultrasonic irradiation is controlled in accordance with the concentration of oxygen as a substance (third substance) contained in the culture solution 3, in addition to the settling velocity of a cell 2. In some embodiments, ultrasonic irradiation may be controlled in accordance with the concentration of a hydrogen ion (pH), or waste matter excreted from cells 2, such as carbon dioxide, ammonia, urea, and lactic acid, as the third substance contained in the culture solution 3. Excessive accumulation of waste matter in the culture solution 3 greatly affects the growth rate of cells 2. When, for example, uneven distribution of waste matter is detected, ultrasonic waves may be emitted to eliminate such uneven distribution of waste matter to create an environment suitable for the growth of cells 2.

Although the acquirer 14 measures the size of a cell 2 based on the image magnification and the diameter or area of the cell 2 in an image in the present embodiment, the acquirer 14 may measure the largest diameter of the cell 2. The acquirer 14 may acquire, as the size of a cell 2, a representative value for the sizes of multiple cells 2, such as an average or a median value.

The detector 13 detects cells 2 based on the degree of similarity between a shape having an edge defined by the boundary and a shape to be determined as the shape of a cell 2. The shape to be determined as a shape of a cell 2 may be the shape of a cell 2, or, for example, a shape similar to the shape of a cell 2, such as a circle, an ellipse, a quadrangle, and a rhombus. When detecting cells 2, the detector 13 performs edge detection to extract the boundary between a cell 2 and the culture solution 3. The detector 13 may use a known image recognition method other than edge detection.

The controller 15 sequentially controls the transducer 10 based on the settling velocity of a cell 2 and on the oxygen concentration in the culture solution 3. In some embodiments, the controller 15 may control the transducer 10 based on the settling velocity of a cell 2 alone. The controller 15 may perform the control based on the settling velocity of a cell 2 and on the oxygen concentration in the culture solution 3 in either order. The controller 15 may use, as a criterion for ultrasonic irradiation, the oxygen concentration in the culture solution 3 in combination with the settling velocity of a cell 2. In this case, for example, the controller 15 emits ultrasonic waves with the transducer 10 when the settling velocity of a cell 2 is higher than or equal to $N_v$ and the oxygen concentration in the culture solution 3 is lower than or equal to $N_{oxy}$.

Although the controller 15 collects cells 2 based on the rate of change in the number of cells 2 in the present embodiment, the user may decide whether to collect cells 2. The cell culture device 100 may not include the cell collection unit 12. The user may instead manually collect cells 2 after a time period during which the cells 2 are likely to grow sufficiently in accordance with the growth characteristics of the cells 2.

Figure 11:
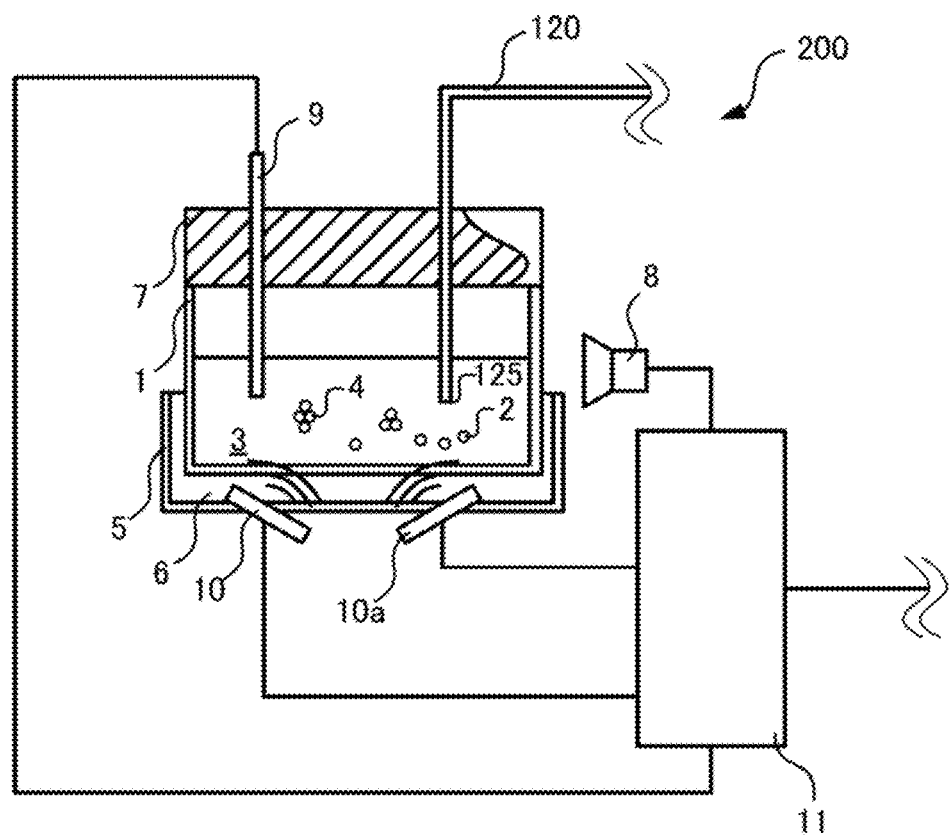
FIG. 11 is a schematic diagram of another example of the cell culture device according to Embodiment 1 of the present disclosure.

A single transducer 10 or multiple transducers 10 may be used. For example, FIG. 11 partially shows components of a cell culture device 200 having the same components as the cell culture device 100 and including an additional transducer 10a of the same type as the transducer 10. The controller 15 controls the transducers 10 and 10a to stir the culture solution 3 more flexibly. For example, the controller 15 causes the transducers 10 and 10a to emit ultrasonic waves alternately.

The transducer 10 may be located on a side surface of the tank 5 instead of on the bottom surface. When multiple transducers 10 are located on a side surface of the tank 5, the transducers 10 may be arranged rotationally symmetrical about the center of the culture vessel 1 as the center of symmetry. When each transducer 10 is located on a side surface as well, the central axis of the ultrasonic waves emitted from the transducer 10 may not be parallel to the bottom surface of the tank 5 to allow ultrasonic irradiation to effectively reduce settling of cells 2.

Embodiment 2

Figure 12:
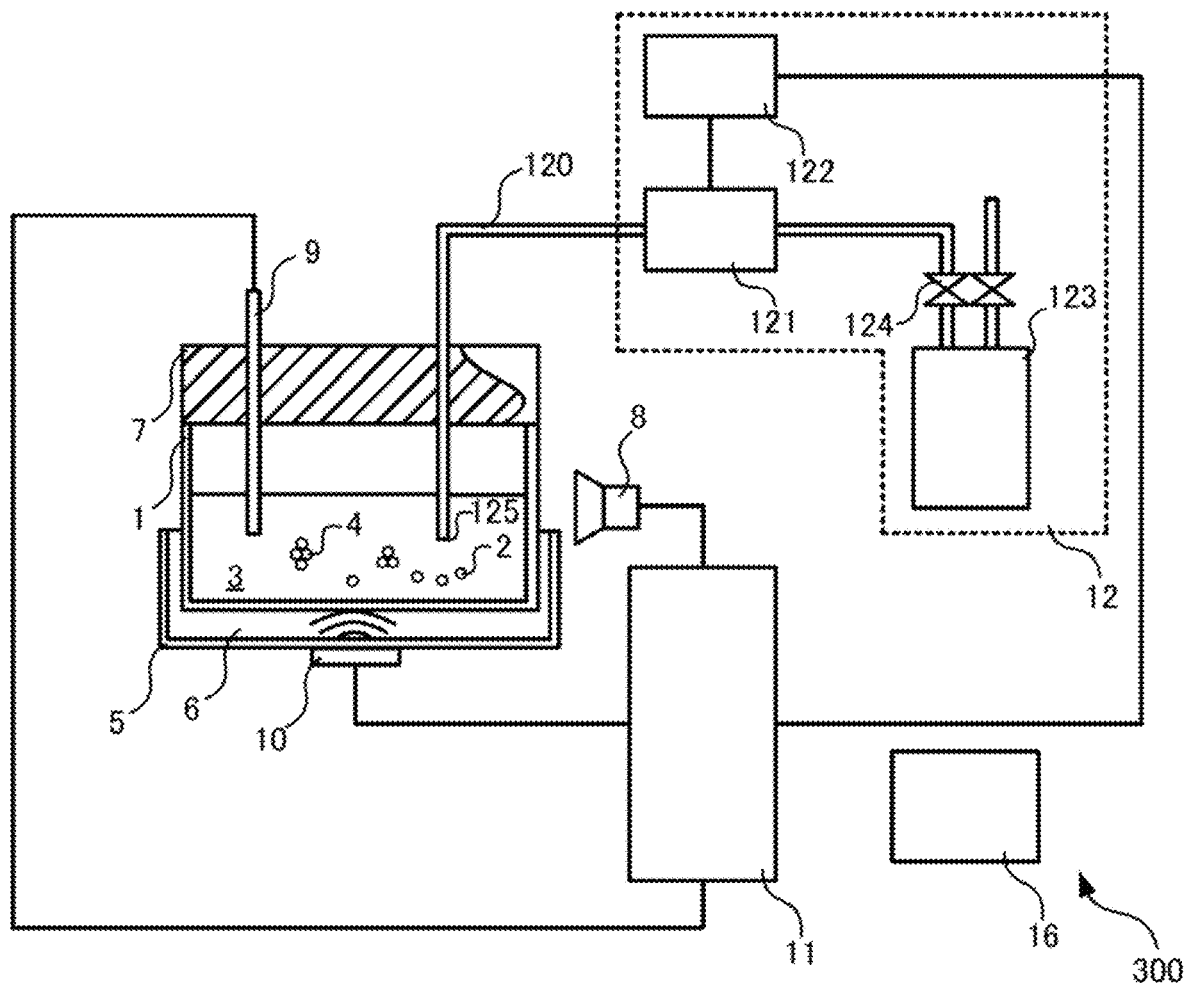
FIG. 12 is a schematic diagram of a cell culture device according to Embodiment 2 of the present disclosure.

A cell culture device 300 according to Embodiment 2 of the present disclosure will now be described focusing on the differences from the cell culture device 100 according to Embodiment 1 described above. As shown in FIG. 12, the cell culture device 300 includes an output unit 16, in addition to the components of the cell culture device 100.

The output unit 16 is connected to the control unit 11. The output unit 16 is controlled by the controller 15. The output unit 16 includes a speaker and generates, from the speaker, a sound for warning or notification based on instruction data transmitted from the controller 15. The warning sound is used to warn that the number of cells 2 in the culture vessel 1 is below a lower limit $N_{min}$. The notification sound is used to notify that the number of cells 2 in the culture vessel 1 has reached an upper limit $N_{max}$. The storage 111 stores $N_{min}$ and $N_{max}$.

Figure 13:
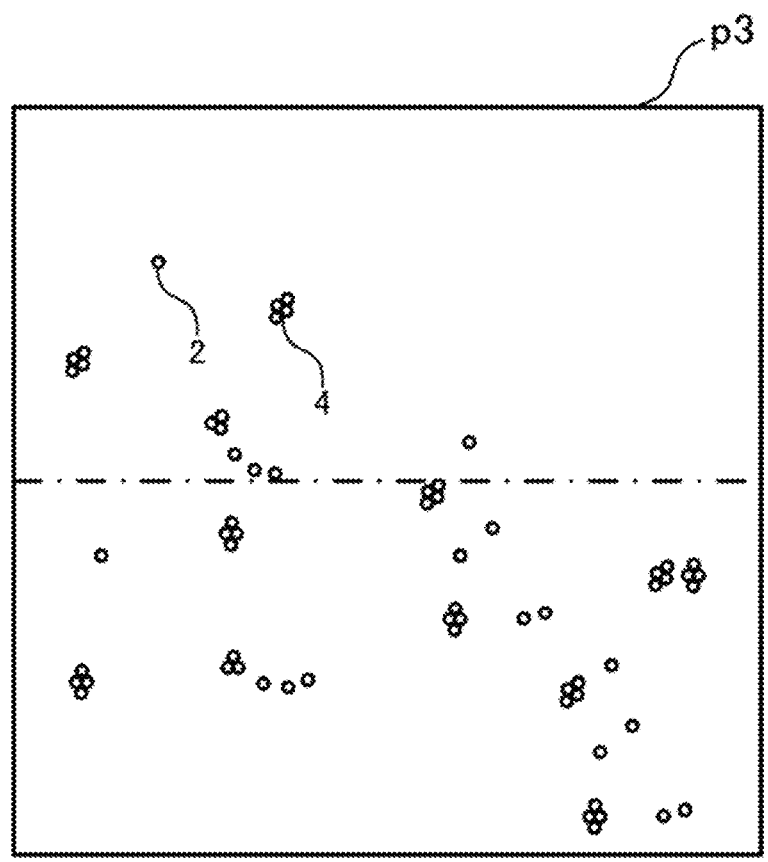
FIG. 13 is a diagram of a captured image of a culture solution.

The acquirer 14 acquires, as information indicating the settling state of cells 2 in the culture vessel 1, the settling degree of cells 2 based on the distribution of cells 2 in the culture vessel 1 detected by the detector 13. The acquirer 14 refers to image data corresponding to an image p3 captured at a time t3 and stored in the storage 111. In FIG. 13, the upper edge of the image p3 corresponds to the liquid level of the culture solution 3 and the lower edge corresponds to the bottom surface of the culture vessel 1. The image p3 thus shows the entire culture solution 3 in the culture vessel 1. The acquirer 14 counts the number N1 of cells 2 detected in the entire image p3 and the number N2 of cells 2 found in an area in the image p3 up to a height set at 50% of the height from the lower edge to the upper edge. The acquirer 14 acquires a value n determined by dividing N2 by N1 as information indicating the settling degree of cells 2. The value n increases as more cells 2 are found near the bottom surface of the culture vessel 1. The acquirer 14 outputs information indicating the value n and N1 to the controller 15.

The acquirer 14 also acquires information correlated with the number of cells 2 in the culture solution 3 detected by the detector 13. The information correlated with the number of cells 2 indicates the number of cells 2 included in the image p3, or specifically, N1 described above. The information correlated with the number of cells 2 may indicate the sum of the areas of cells 2 in the image or the concentration of cells 2.

The controller 15 provides a notification to the user based on the information correlated with the concentration of cells 2. In more detail, the controller 15 compares N1 with $N_{min}$ and $N_{max}$ prestored in the storage 111. When N1 is less than or equal to $N_{min}$, cells 2 may have grown insufficiently and the culture condition may be unsuitable for the cells 2. When N1 is less than or equal to $N_{min}$, the controller 15 outputs a warning sound with the output unit 16. When N1 is greater than or equal to $N_{max}$, cells 2 have grown sufficiently and the controller 15 outputs, with the output unit 16, a notification sound different from the warning sound.

The controller 15 controls the operation of the transducer 10 based on the information indicating the settling degree of cells 2. The controller 15 compares the value n with a threshold N0 prestored in the storage 111. When the value n is greater than or equal to N0, the settling degree is high and cells 2 may be difficult to grow without being suspended. Thus, when the value n is greater than or equal to the threshold, the controller 15 emits, with the transducer 10, ultrasonic waves toward the culture solution 3.

The controller 15 collects cells 2 based on the information indicating the settling state of cells 2, or specifically, the rate of change in the value n. The controller 15 calculates the rate of change in the value n based on the value n determined for the image p3 and the value n determined in the same manner for an image p4 captured t minutes before the capturing of the image p3. The controller 15 compares the rate of change in the value n with a threshold Nc prestored in the storage 111. When the rate of change in the value n is lower than or equal to Nc, the settling degree of cells 2 remains nearly unchanged. This indicates that the distribution of cells 2 remains unchanged and the cells 2 have grown sufficiently. The controller 15 thus instructs the suction pump controller 122 to collect cells 2. In response to the instruction from the controller 15, the suction pump controller 122 collects cells 2. When the rate of change in the value n is higher than Nc, cells 2 in an exponential growth phase are yet to grow sufficiently. The controller 15 thus continues to culture cells 2, without collecting cells 2.

Figure 14:
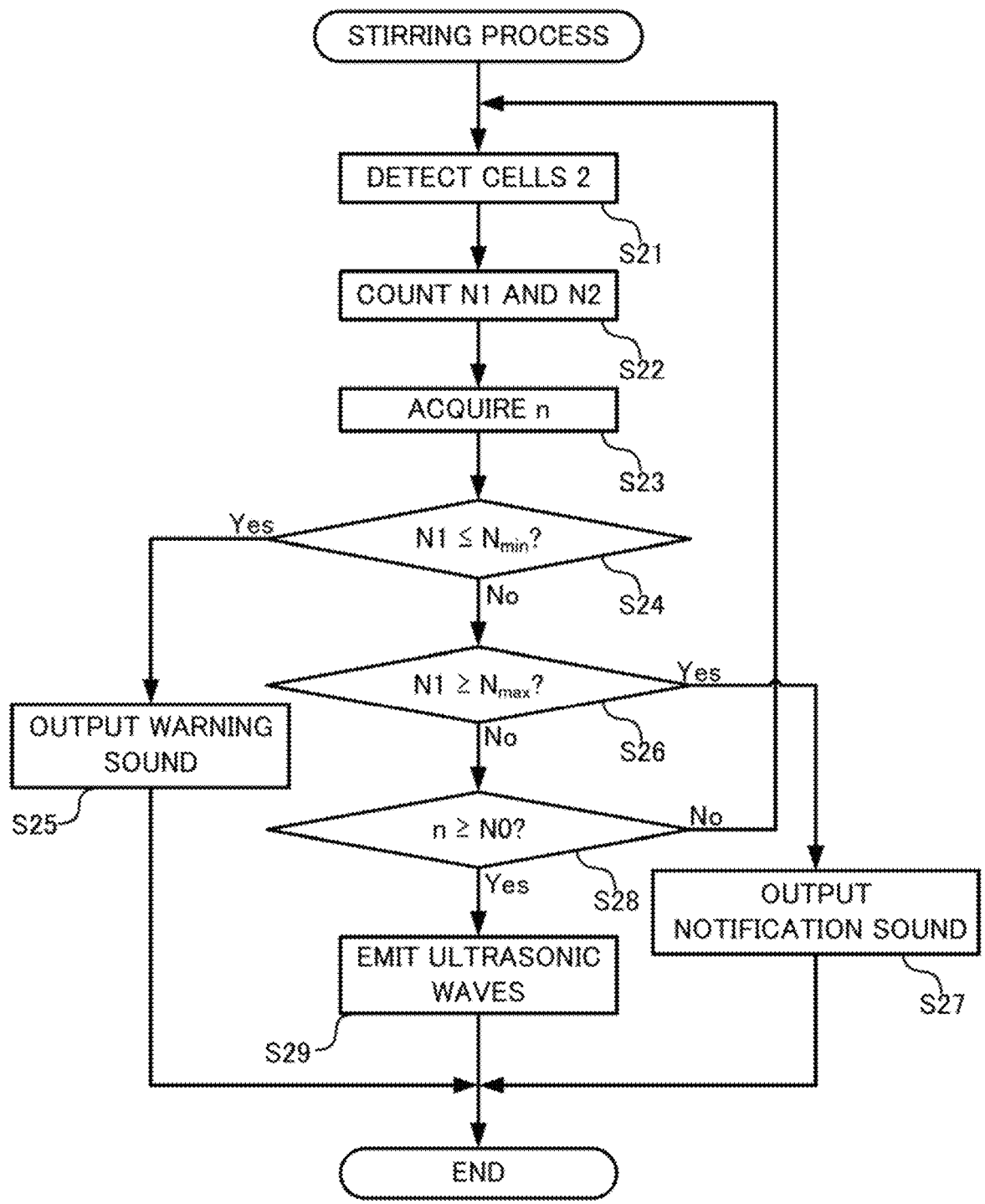
FIG. 14 is a flowchart of a stirring process performed by the cell culture device shown in FIG. 12.

The operation of the cell culture device 300 according to the present embodiment will now be described. FIG. 14 is a flowchart of a stirring process performed by the cell culture device 300. During culturing, the detector 13 detects cells 2 in the culture solution 3 (step S21). The acquirer 14 counts N1 and N2 (step S22). The acquirer 14 then acquires a value of n (step S23). The controller 15 determines whether N1 is less than or equal to $N_{min}$ (step S24). When N1 is less than or equal to $N_{min}$ (Yes in step S24), the controller 15 outputs a warning sound with the output unit 16 (step S25) and ends the stirring process.

When N1 is greater than $N_{min}$ (No in step S24), the controller 15 determines whether N1 is greater than or equal to $N_{max}$ (step S26). When N1 is greater than or equal to $N_{max}$ (Yes in step S26), the controller 15 outputs a notification sound with the output unit 16 (step S27) and ends the stirring process.

When N1 is less than $N_{max}$ (No in step S26), the controller 15 determines whether the value n is greater than or equal to NO (step S28). When the value n is greater than or equal to NO (Yes in step S28), the controller 15 emits, with the transducer 10, ultrasonic waves toward the culture solution 3 (step S29) and ends the stirring process. When the value n is less than NO (No in step S28), the controller 15 returns to step S21.

Figure 15:
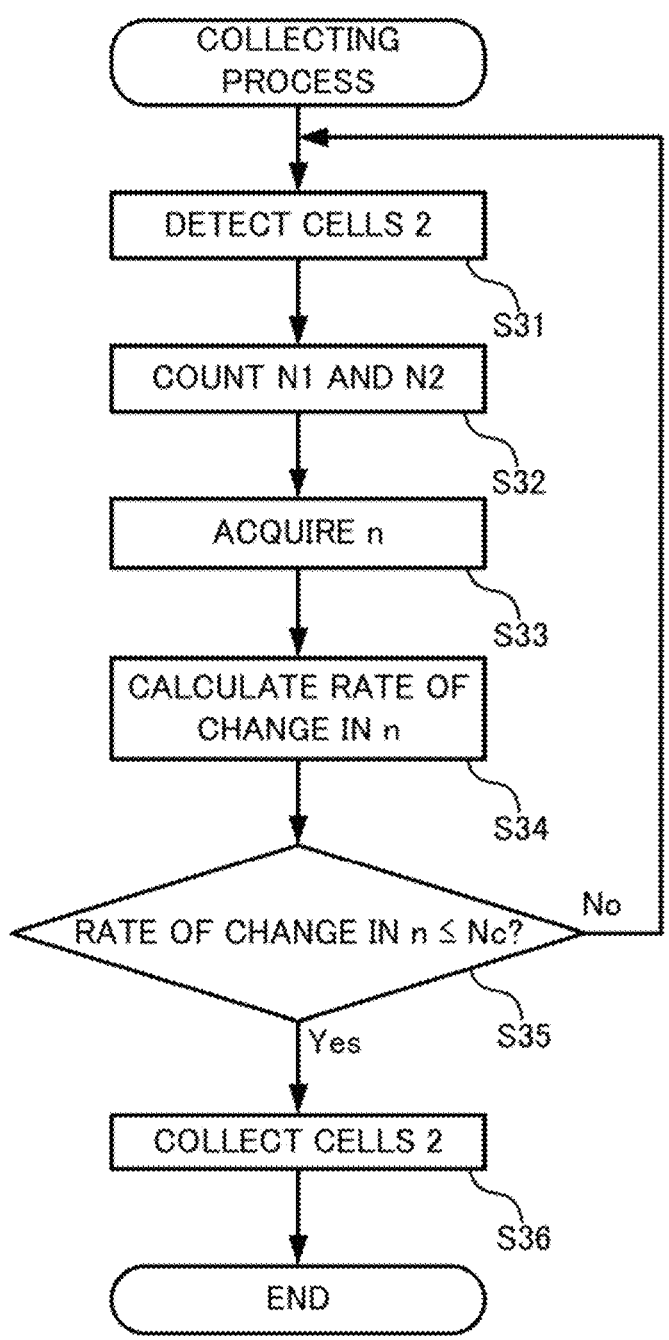
FIG. 15 is a flowchart of a collecting process performed by the cell culture device shown in FIG. 12.

A process of collecting cells 2 with the cell culture device 300 will now be described with reference to FIG. 15. The detector 13 performs step S21 as step S31, and the acquirer 14 performs steps S22 and S23 as steps S32 and S33. Subsequently, the controller 15 calculates the rate of change in the value n (step S34). The controller 15 determines whether the rate of change in the value n is lower than or equal to Nc (step S35). When the rate of change in the value n is lower than or equal to Nc (Yes in step S35), the controller 15 collects cells 2 with the cell collection unit 12 (step S36) and ends the culturing process. In this manner, the cells 2 are collected in the collection bag 123. When the rate of change in the value n is higher than Nc (No in step S35), the controller 15 returns to step S31.

As described above, the cell culture device 300 according to the present embodiment allows ultrasonic irradiation when the settling degree of cells 2 in the culture vessel 1 is high and allows no ultrasonic irradiation when the settling degree is low. This allows cells 2 settling in the culture solution 3 to be suspended, thus maintaining an optimal condition for culturing cells 2.

The cell culture device 300 outputs a warning sound when the number N1 of cells 2 detected in the image p3 is less than or equal to $N_{min}$. In this manner, the user can learn that the growth of cells 2 is not facilitated and the condition is inappropriate for culturing cells 2. When the number N1 of cells 2 is greater than or equal to $N_{max}$, a notification sound is output. The number N1 greater than or equal to $N_{max}$ indicates that cells 2 have been grown sufficiently. In response to the notification sound, the user can exchange the culture solution 3 or collect cells 2. The output unit 16 may include, in addition to or in place of the speaker, an indicator lamp. In this case, the output unit 16 illuminates the indicator lamp in accordance with instruction data transmitted from the controller 15.

The cell culture device 300 collects cells 2 based on the information indicating the settling state of cells 2. This allows timely collection of cells 2 when the cells 2 have grown sufficiently.

The user may conduct a preparatory experiment in accordance with the culture vessel 1, cells 2 to be cultured, and the culture solution 3 to determine $N_{max}$, $N_{min}$, and Nc in any manner. Although N2 is acquired by counting the number of cells 2 found in an area in the image p3 up to a height set at 50% of the height from the lower edge to the upper edge in the present embodiment, the set height is adjusted as appropriate in accordance with the type of cells 2.

The acquirer 14 acquires, as information indicating the settling degree of cells 2, the ratio n of the number N2 of cells 2 found in an area in the image p3 up to the height set at 50% of the height from the lower edge to the upper edge to the number N1 of cells 2 detected in the entire image p3. In some embodiments, the acquirer 14 may acquire, as information indicating the settling degree of cells 2, the ratio of the areas of cells 2 found in an area in the image p3 from the lower edge up to a predetermined height to the areas of cells 2 detected in the entire image p3. In the process of collecting cells 2, the controller 15 determines whether the rate of change in the value n is lower than or equal to Nc.

In some embodiments, the controller 15 may collect cells 2 based on the ratio of the areas of cells 2 found in an area in the image p3 from the lower edge up to a predetermined height to the areas of cells 2 detected in the entire image p3.

The controller 15 may further adjust the duration for ultrasonic irradiation by the transducer 10 in accordance with the settling velocity of a cell 2. When ultrasonic irradiation is performed in the stirring process in the present embodiment, the controller 15 may adjust the duration for ultrasonic irradiation based on the size of a cell 2.

Although the stirring process and the collecting process are independently performed in the present embodiment, the collecting process may be sequentially performed after the stirring process. For example, when the value n is less than NO (No in step S28) in the stirring process, the controller 15 may advance to step S34 in the collecting process. This allows timely collection of cells 2 when the settling degree is low in the culture solution 3 saturated with the cells 2.

With the cell culture device 300, step S23 in the stirring process may be followed by the processing in step S34 and subsequent steps in the collecting process in parallel with steps S24 to S29.

Embodiment 3

Figure 16:
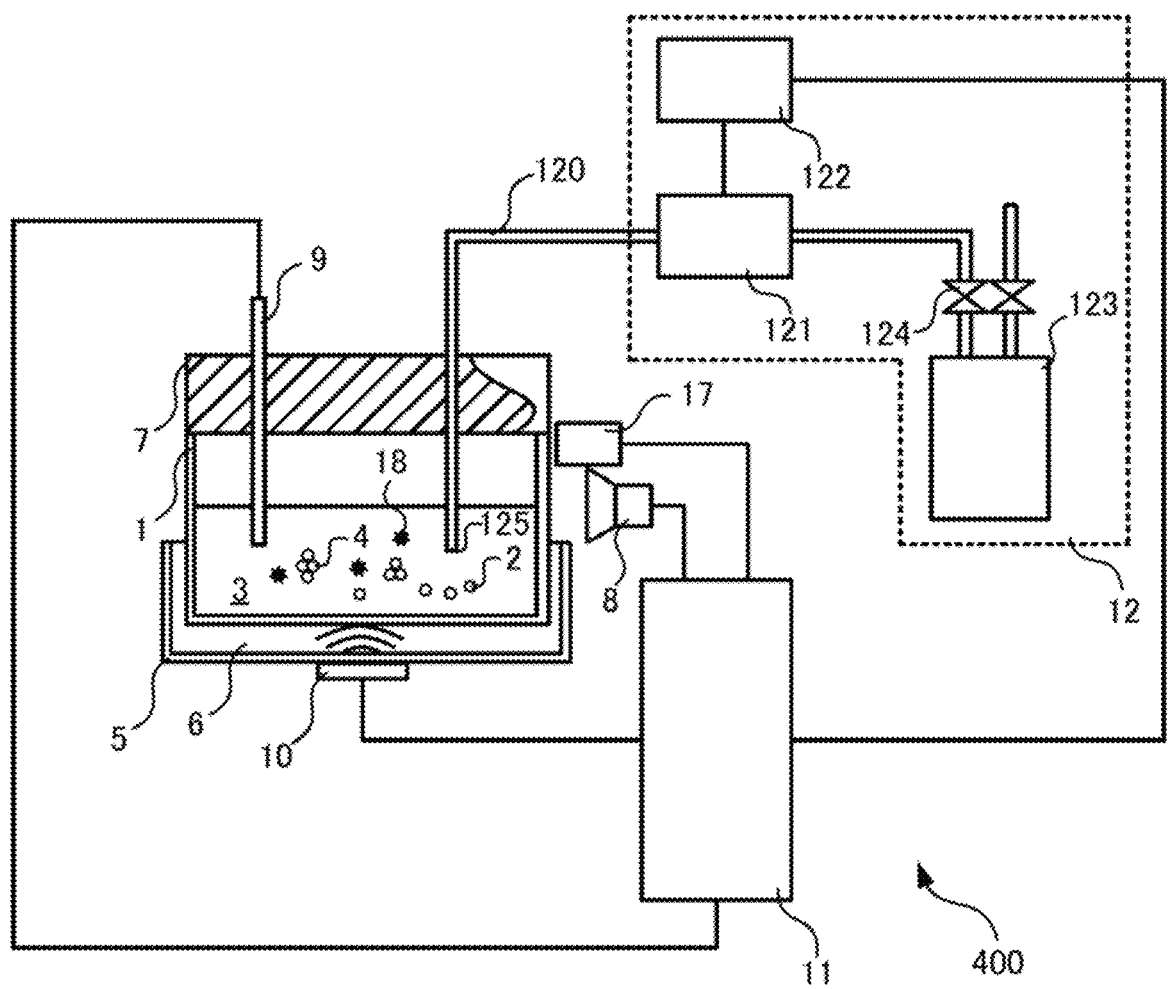
FIG. 16 is a schematic diagram of a cell culture device according to Embodiment 3 of the present disclosure.

As shown in FIG. 16, a cell culture device 400 according to Embodiment 3 of the present disclosure further includes a light source 17, in addition to the components of the cell culture device 100 according to Embodiment 1 described above. The cell culture device 400 will now be described focusing on the differences from the cell culture device 100 according to Embodiment 1 described above.

The cell culture device 400 further includes the light source 17 connected to the control unit 11. As controlled by the controller 15, the light source 17 irradiates the entire culture vessel 1 with excitation light such as ultraviolet rays.

The culture solution 3 contains a fluorescent substance 18. The fluorescent substance 18 has the same specific gravity and substantially the same volume as the cell 2. The fluorescent substance 18 thus has the same distribution as cells 2 in the culture solution 3. The same distribution herein refers to a state in which the culture solution 3 contains the same number of cells 2 and pieces of the fluorescent substance 18, and substantially the same number of cells 2 and pieces of the fluorescent substance 18 are contained in the culture solution 3 taken from any position in the culture vessel 1 immediately after the culture solution 3 is stirred. When receiving excitation light, the fluorescent substance 18 emits light.

The light source 17 emits excitation light in a wavelength range that does not overlap the wavelength range of the light emitted from the fluorescent substance 18. The optical sensor 8 includes a light receiving element appropriate for the wavelength of the light emitted from the fluorescent substance 18.

The detector 13 detects the fluorescent substance 18 contained in the culture solution 3. In more detail, the detector 13 detects, using edge detection, the fluorescent substance 18 in an image from image data corresponding to the image including cells 2 and the culture solution 3 captured by the optical sensor 8, with the culture vessel 1 being irradiated with excitation light by the light source 17. The detector 13 associates the image data with positional information for the fluorescent substance 18 in the image corresponding to the image data, and stores the data and information into the storage 111.

Figure 17:
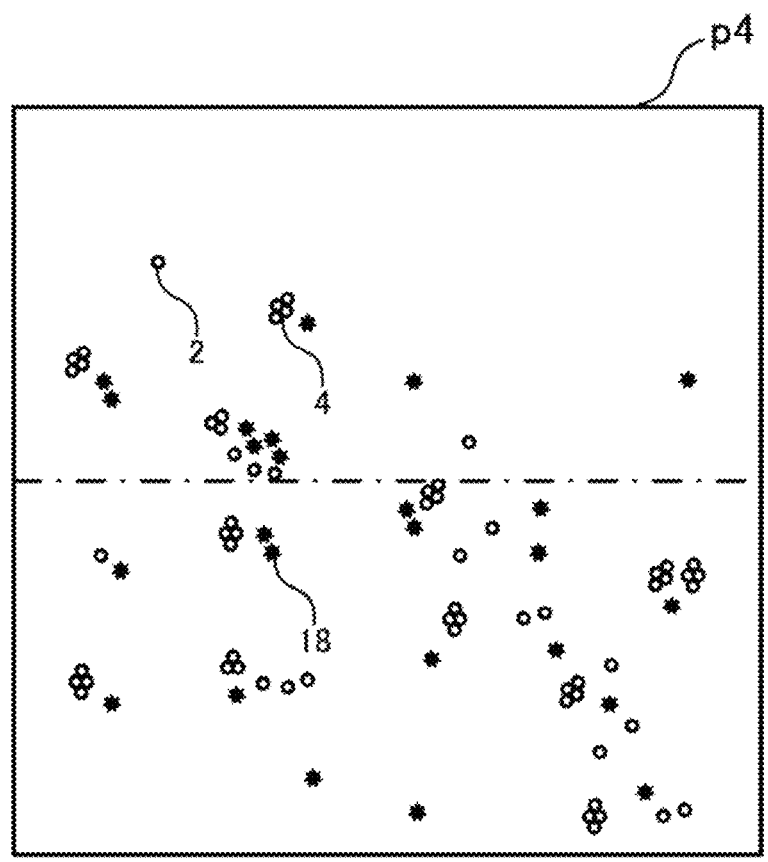
FIG. 17 is a diagram of a captured image of a culture solution containing a fluorescent substance.

The acquirer 14 acquires, as information indicating the settling state of cells 2, information indicating the settling degree of the fluorescent substance 18 in the culture vessel 1 based on the distribution of the fluorescent substance 18 in the culture vessel 1 detected by the detector 13. The acquirer 14 first refers to the image data stored in the storage 111. The image p4 shown in FIG. 17 captured at a time t4 shows the entire culture solution 3 in the same manner as the image p3 described above. The acquirer 14 counts the number N3 of pieces of the fluorescent substance 18 detected in the entire image p4 and the number N4 of pieces of the fluorescent substance 18 found in an area in the image p4 up to a height set at 50% of the height from the lower edge to the upper edge. The acquirer 14 acquires a value m determined by dividing N4 by N3 as information indicating the settling degree of the fluorescent substance 18. The fluorescent substance 18 has the same distribution as cells 2 in the culture solution 3. Thus, the information indicating the settling degree of the fluorescent substance 18 may be used as information indicating the settling state of cells 2.

The controller 15 compares the value m with a threshold $N_m$ prestored in the storage 111. The controller 15 determines whether the value m is greater than or equal to $N_m$. When m is greater than or equal to $N_m$, the controller 15 emits, with the transducer 10, ultrasonic waves toward the culture vessel 1.

Figure 18:
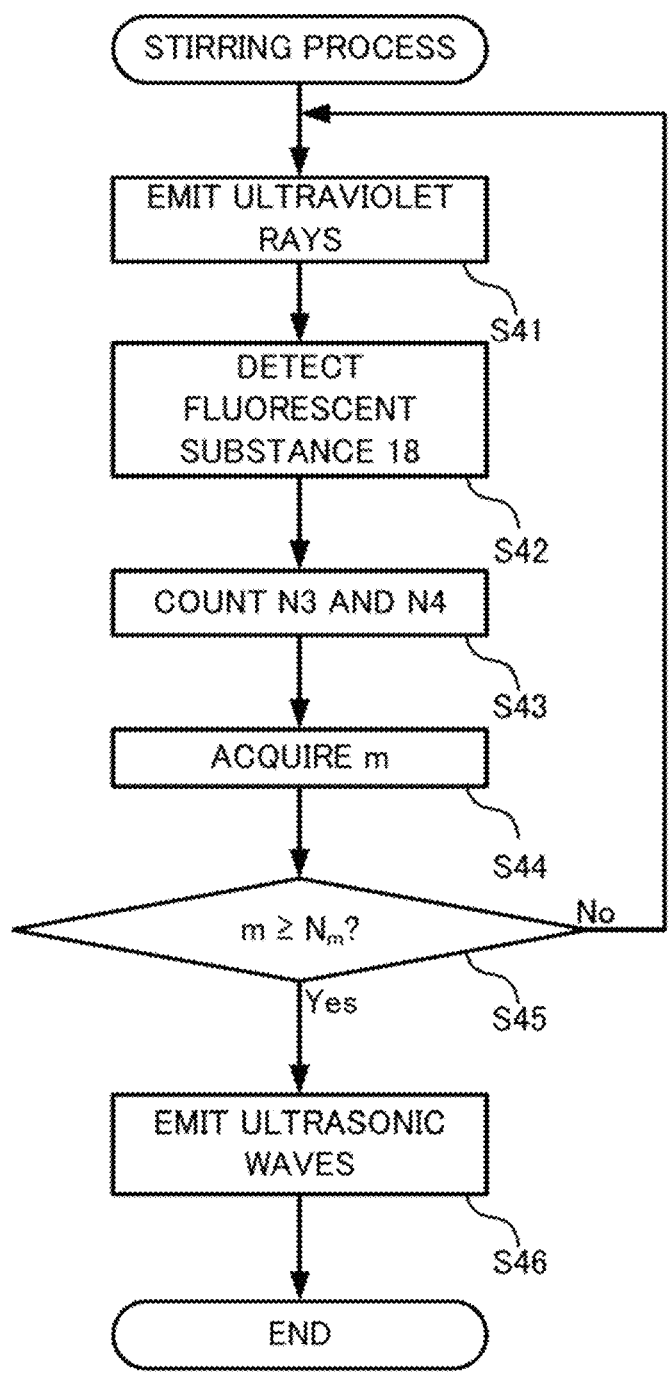
FIG. 18 is a flowchart of a stirring process performed by the cell culture device shown in FIG. 16.

A stirring process performed by the cell culture device 400 will now be described with reference to the flowchart shown in FIG. 18. At least $10^7$ cells 2 are seeded in the culture solution 3 and the fluorescent substance 18 is added to the culture solution 3. When a predetermined time period has elapsed after the start of culturing, the controller 15 irradiates the culture vessel 1 with excitation light emitted from the light source 17 (step S41). The detector 13 detects the fluorescent substance 18 in the culture solution 3 (step S42). The acquirer 14 counts N3 and N4 (step S43).

The acquirer 14 then acquires a value m (step S44). The controller 15 determines whether the value m is greater than or equal to $N_m$ (step S45). When the value m is greater than or equal to $N_m$ (Yes in step S45), the controller 15 emits, with the transducer 10, ultrasonic waves toward the culture solution 3 (step S46) and ends the stirring process. When the value m is less than $N_m$ (No in step S45), the controller 15 returns to step S41.

As described above, the cell culture device 400 according the present embodiment can indirectly acquire information indicating the settling state of cells 2 in the culture vessel 1 by acquiring information indicating the settling degree of the fluorescent substance 18 that has the same distribution as cells 2 in the culture vessel 1. The light emitted from the fluorescent substance 18 in response to irradiation with excitation light is easily detectable. The distribution of cells 2 can thus be estimated accurately. Ultrasonic irradiation is performed when the settling degree of cells 2 in the culture vessel 1 that is determined based on the positions of pieces of the fluorescent substance 18 is high. This allows settling cells 2 to be suspended, thus maintaining an optimal condition for culturing cells 2.

Similarly to the cell culture device 300 described above, the cell culture device 400 according to the present embodiment may output a warning sound and a notification sound based on the number N1 of cells 2 detected in the image p3. Instead of outputting a warning sound and a notification sound, the cell culture device 400 may illuminate an indicator lamp based on the number N1 of cells 2 detected. Similarly to the cell culture device 300 described above, the cell culture device 400 according to the present embodiment may collect cells 2 based on the rate of change in the value n.

When irradiation with excitation light by the light source 17 damages or deteriorates cells 2, irradiation with excitation light by the light source 17 may not be performed constantly but may be performed in synchronization with capturing an image by the optical sensor 8.

Although N4 is acquired by counting the number of cells 2 found in an area in the image p4 up to a height set at 50% of the height from the lower edge to the upper edge in the present embodiment, the set height may be set as appropriate in accordance with the type of cells 2.

A substance (first substance) having the same distribution as cells 2 is not limited to the fluorescent substance 18. Such substances may include, for example, a fluorochrome-containing substance that is absorbable onto surfaces of cells 2 and a marker substance or a luminous substance that can be taken in cells 2 and does not affect the growth of the cells 2.

Embodiment 4

A cell culture device 500 according to Embodiment 4 of the present disclosure has the same structure as the cell culture device 100 according to Embodiment 1 described above. For the structure of the cell culture device 500, FIG. 1 is referred to with the cell culture device 100 replaced with the cell culture device 500. The cell culture device 500 will now be described focusing on the differences from the cell culture device 100.

Cells 2 consume oxygen as they grow. Thus, in the culture solution 3, the concentration of cells 2 is high in an area in which the oxygen concentration is low, whereas the concentration of cells 2 is low in an area in which the oxygen concentration is high. In other words, the concentration of cells 2 is inversely proportional to the oxygen concentration in the culture solution 3. The distribution of cells 2 in the culture vessel 1 can thus be indirectly acquired by measuring the distribution of oxygen concentrations in the culture solution 3. The cell culture device 500 controls ultrasonic irradiation based on the distribution of oxygen concentrations in the culture solution 3.

Indigo carmine is used to measure the oxygen concentration in the culture solution 3. Indigo carmine is blue when dissolved in water, and turns green when combined with oxygen under a neutral condition due to the absorptivity at a wavelength of 550 nm. When cells 2 are cultured in the culture solution 3 containing indigo carmine, an area colored green has a higher oxygen concentration than an area colored blue. In other words, an area colored blue has a higher concentration of cells 2 than an area colored green.

The detector 13 detects oxygen distributed in the culture solution 3 in accordance with the distribution of cells 2 in the culture solution 3. The detector 13 detects, using a known color analysis technique, an area colored blue in an image captured by the optical sensor 8.

The detector 13 associates image data with positional information for the blue-colored area in the image corresponding to the image data, and stores the data and information into the storage 111.

The acquirer 14 refers to the image data stored in the storage 111. The image corresponding to the image data shows the entire culture solution 3 in the same manner as the image p3 described above. The acquirer 14 acquires, as information indicating the settling state of cells 2, the ratio r of blue-colored areas in an area in the image up to a height set at 50% of the height from the lower edge to the upper edge. The ratio r is information indicating the oxygen distribution in the culture solution 3.

The controller 15 compares the ratio r with a threshold B prestored in the storage 111. The controller 15 determines whether the ratio r is greater than or equal to B. When the ratio r is greater than or equal to B, the controller 15 emits, with the transducer 10, ultrasonic waves toward the culture solution 3.

Figure 19:
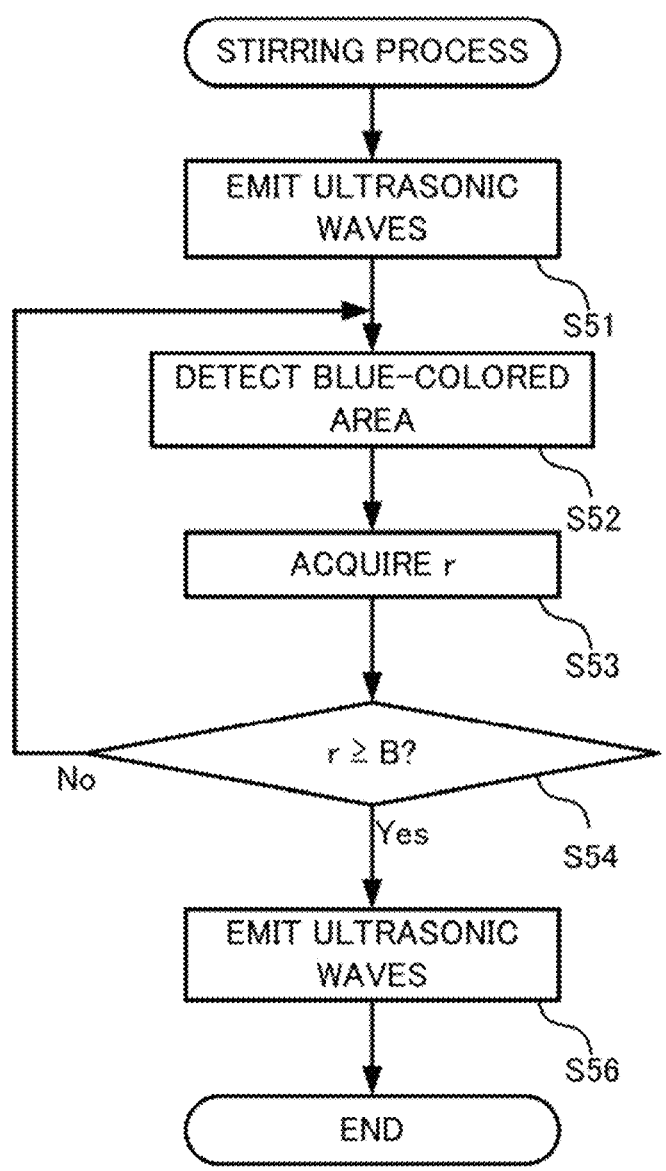
FIG. 19 is a flowchart of a stirring process performed by a cell culture device according to Embodiment 4 of the present disclosure.

A stirring process performed by the cell culture device 500 will now be described with reference to the flowchart shown in FIG. 19. At least $10^7$ cells 2 are seeded in the culture solution 3, and indigo carmine in a concentration of 0.1% by weight is added to the culture solution 3. The controller 15 first emits, with the transducer 10, ultrasonic waves toward the culture vessel 1 (step S51). This produces acoustic streaming in the culture solution 3 resulting from acoustic radiation pressure. The acoustic streaming disperses the cells 2 within the culture solution 3. After the transducer 10 stops operating, the cells 2 settle gradually with time to the bottom surface of the culture vessel 1. Thus, the culture solution 3 is colored with more blue at the bottom in the culture solution 3 than at around the liquid level of the culture solution 3.

The detector 13 detects an area colored blue in an image captured by the optical sensor 8 (step S52). The acquirer 14 then acquires a ratio r (step S53). The controller 15 determines whether the ratio r is greater than or equal to B (step S54). When the ratio r is greater than or equal to B (Yes in step S54), the controller 15 emits, with the transducer 10, ultrasonic waves toward the culture solution 3 (step S55) and ends the stirring process. The ultrasonic irradiation disperses the cells 2 through the entire culture solution 3. When the ratio r is less than B (No in step S54), the controller 15 returns to step S52.

As described above, the cell culture device 500 according the present embodiment can indirectly acquire information about the positions of cells 2 in the culture vessel 1 by acquiring information indicating an area with a low concentration of oxygen distributed in the culture solution 3 in accordance with the distribution of cells 2 in the culture vessel 1. The distribution of cells 2 in the culture vessel 1 can be determined by using a substance that is more easily detectable than cells 2 when the cells 2 are detected directly.

The substance (second substance) distributed in the culture solution 3 in accordance with the distribution of cells 2 in the culture solution 3 may be, for example, a substance that increases in proportion to the concentration of cells 2, or a substance that increases in inverse proportion to the concentration of cells 2. Although oxygen is detected using indigo carmine as a substance distributed in the culture solution 3 in accordance with the distribution of cells 2 in the present embodiment, the distribution of the concentration of hydrogen ions, or pH, in the culture solution 3 may be detected. When phenolphthalein is used as a pH indicator for example, a solution with a pH value of greater than or equal to 8.3 is normally red, whereas the solution near a cell 2 is acidified and is thus colorless. A colorless area thus indicates the presence of a large number of cells 2. In this case, the detector 13 detects the pH distributed in the culture solution 3 in accordance with the distribution of cells 2 in the culture solution 3. Then, the acquirer 14 acquires, as information indicating the settling state of cells 2, the ratio of colorless areas in an area in the image up to a height set at 50% of the height from the lower edge to the upper edge.

Although indigo carmine in a concentration of 0.1% by weight is added to the culture solution 3 in the present embodiment, the concentration of indigo carmine may be adjusted as appropriate.

Figure 20:
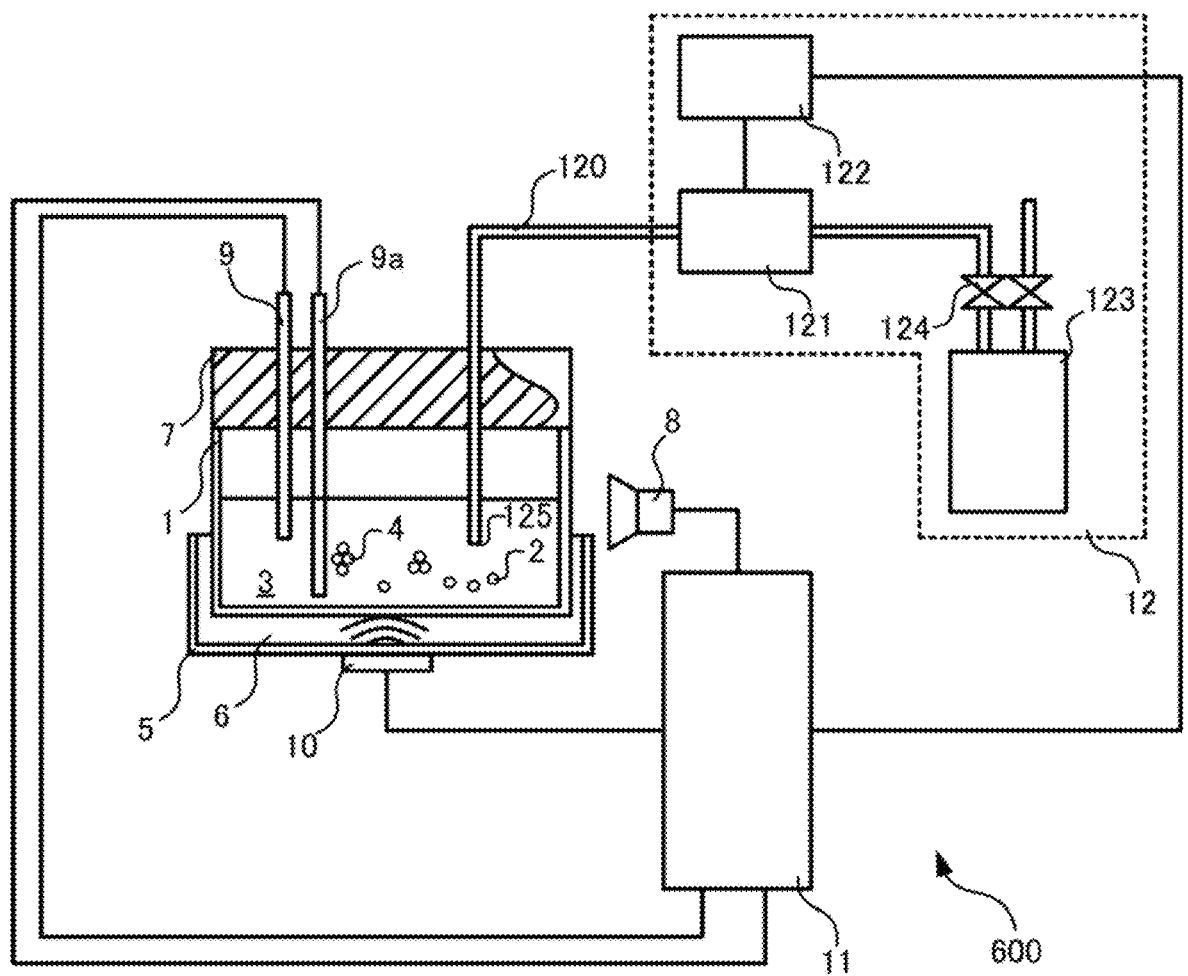
FIG. 20 is a schematic diagram of another example of the cell culture device according to Embodiment 4 of the present disclosure.

In another embodiment, the culture solution sensor 9, in place of the optical sensor 8, is used to detect a substance distributed in the culture solution 3 in accordance with the distribution of cells 2 in the culture solution 3. For example, as shown in FIG. 20, a cell culture device 600 includes a culture solution sensor 9a in addition to the components of the cell culture device 100. The culture solution sensor 9 measures the pH in an upper part of the culture solution 3. The culture solution sensor 9a measures the pH in a lower part of the culture solution 3. Information indicating the pH measured by the culture solution sensors 9 and 9a is transmitted to the control unit 11. When the pH indicates higher acidity in the lower part than in the upper part in the culture solution 3, the controller 15 may emit ultrasonic waves toward the culture solution 3. The cell culture device 600 can thus easily prevent settling of cells 2 in the culture vessel 1.

The culture solution sensors 9 and 9a may each be an electrode that can measure pH or oxygen concentration. The culture solution sensors 9 and 9a may each be a sensor that can measure waste matter excreted from cells 2. The cell culture device 600 may additionally have functions described in other embodiments.

Embodiment 5

Figure 21:
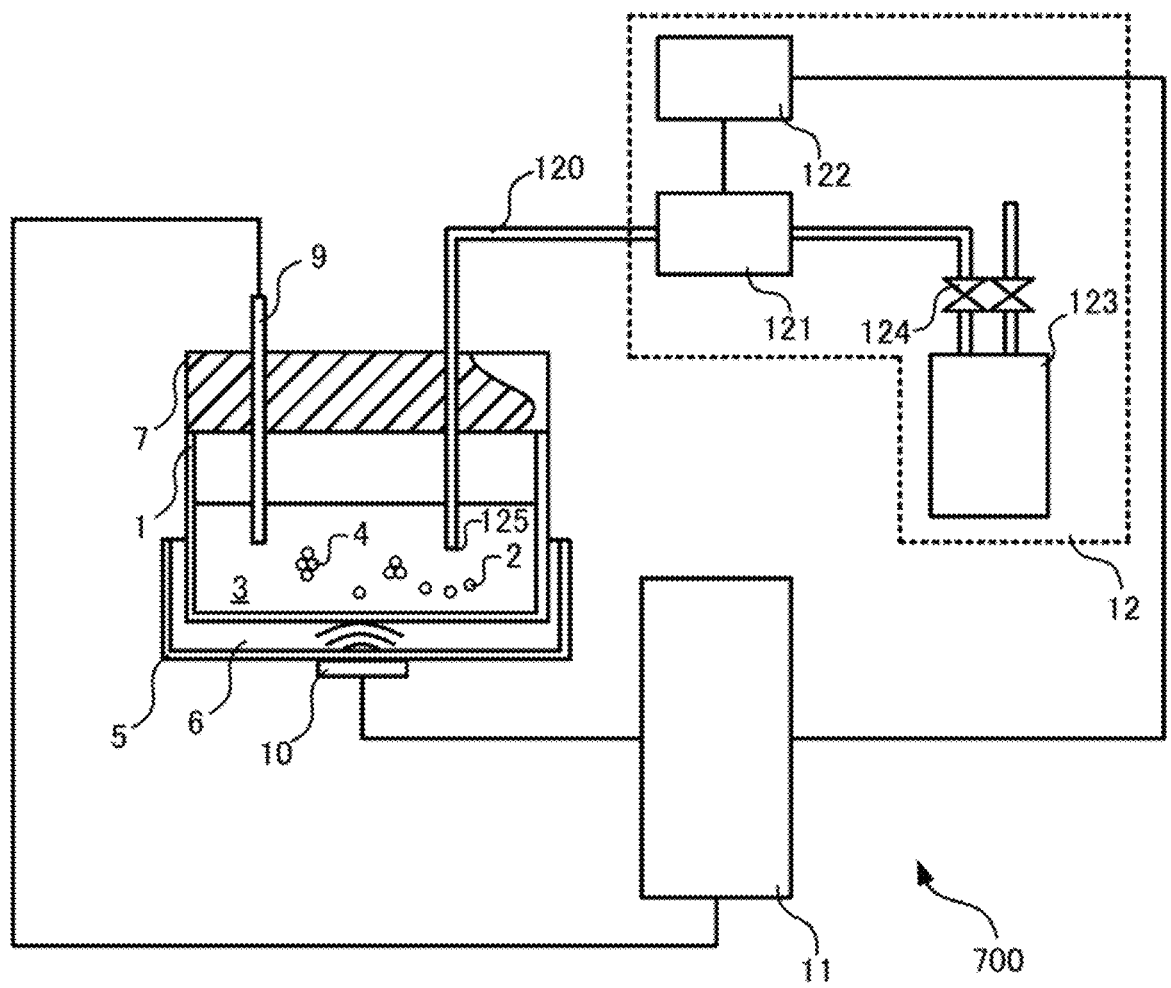
FIG. 21 is a schematic diagram of a cell culture device according to Embodiment 5 of the present disclosure.

As shown in FIG. 21, a cell culture device 700 according to Embodiment 5 of the present disclosure has the same structure as the cell culture device 100 except that the cell culture device according to Embodiment 5 does not include the optical sensor 8. The cell culture device 700 will now be described focusing on the differences from the cell culture device 100 according to Embodiment 1 described above.

The acquirer 14 calculates the terminal velocity of a cell 2 as information indicating the settling state. The terminal velocity herein refers to a velocity that becomes constant when a body force and a drag that depends on velocity acting on a cell 2 are balanced with each other. The terminal velocity is calculated using the Stokes' equation (formula 1) based on the initial distribution state of cells 2 in an observation. The Stokes' equation expresses a terminal velocity of a small particle falling in a fluid.

$$V_s = D_p^2 (\rho_p - \rho_r) \cdot g / 18\eta \qquad \text{(formula 1)}$$

where $V_s$ is the terminal velocity (m/s), $D_p$ is the diameter of the particle (m), $\rho_p$ is the density of the particles (kg/m$^3$), $\rho_r$ is the density of the fluid (kg/m$^3$), g is the gravitational acceleration (m/s$^2$), and $\eta$ is the viscosity of the fluid (Pa·s).

The values $D_p$, $\rho_p$, $\rho_r$, g, and $\eta$ are predetermined based on a preparatory experiment or theoretical values. The acquirer 14 can calculate the time taken for a cell 2 to settle based on the terminal velocity $V_s$ calculated based on preliminarily given values of $D_p$, $\rho_p$, $\rho_r$, g, and $\eta$ and the height of the culture solution 3. The initial distribution state of cells 2 in an observation herein refers to the distribution of cells 2 in the culture solution 3 immediately after the start of culturing or immediately after stirring the culture solution 3. The cells 2 are distributed evenly in the culture vessel 1 in the initial distribution state.

When a predetermined time period has elapsed after cells 2 are in the initial distribution state, the cells 2 in the culture solution 3 settle at a constant settling velocity. Thus, the acquirer 14 can estimate the distribution of cells 2 over time. The controller 15 emits ultrasonic waves to the culture solution 3 with the transducer 10 at a time when the cells 2 start settling based on the estimated distribution of cells 2.

The ultrasonic irradiation suspends the settling cells 2, thus preventing excessive settling of cells 2 in the culture vessel 1.

As described above, the cell culture device 700 according to the present embodiment can acquire information indicating the settling state without the optical sensor 8. The cell culture device 700 thus has a simplified structure and cultures cells 2 efficiently while preventing excessive ultrasonic irradiation to the culture solution 3 in stirring the solution using ultrasonic waves.

The cell culture device 700 may not include the culture solution sensor 9. The cell culture device 700 may include the optical sensor 8 and additionally have functions described in other embodiments.

Embodiment 6

Figure 22:
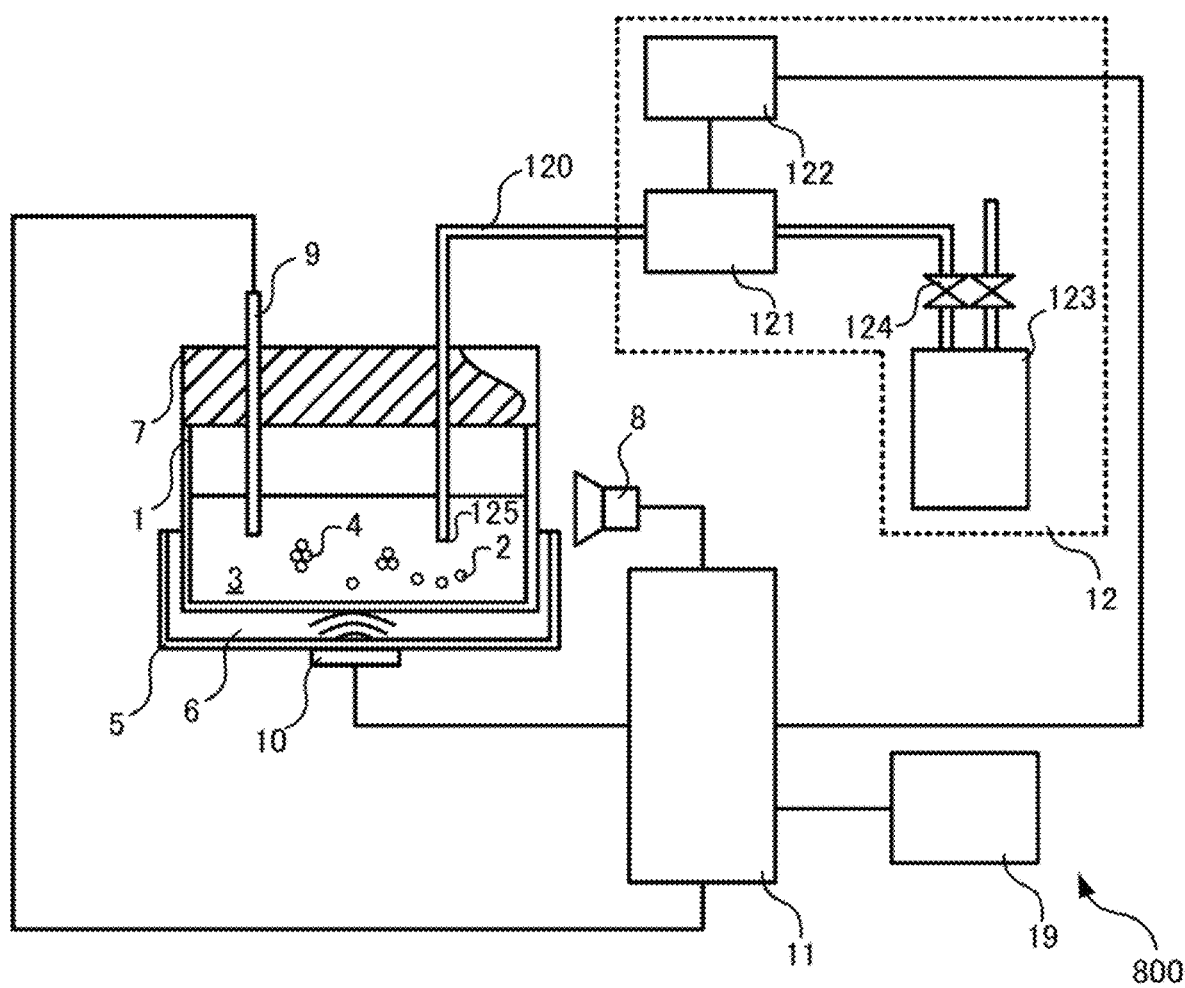
FIG. 22 is a schematic diagram of a cell culture device according to Embodiment 6 of the present disclosure.

A cell culture device 800 according to Embodiment 6 of the present disclosure will now be described focusing on the differences from the cell culture device 100 according to Embodiment 1 described above. As shown in FIG. 22, the cell culture device 800 includes a vessel information setting unit 19 in addition to the components of the cell culture device 100.

The vessel information setting unit 19 includes an input unit for the user to input information about the capacity of the culture vessel 1. The vessel information setting unit 19 is connected to the control unit 11. The vessel information setting unit 19 transmits, to the control unit 11, information about the culture vessel 1 input by the user with the input unit.

The information about the culture vessel 1 herein refers to the height and the bottom area of the culture vessel 1. The acquirer 14 calculates, as information about the capacity of the culture vessel 1, the capacity of the culture vessel 1 based on the height and the bottom area of the culture vessel 1. The controller 15 controls the operation of the transducer 10 in accordance with the capacity of the culture vessel 1. The controller 15 adjusts the duration for ultrasonic irradiation based on the capacity of the culture vessel 1. For example, when the capacity of the culture vessel 1 is greater than or equal to a threshold C prestored in the storage 111, the controller 15 emits ultrasonic waves for a duration T1. When the capacity of the culture vessel 1 is less than C, the controller 15 emits ultrasonic waves for a duration T2 shorter than T1.

Figure 23:
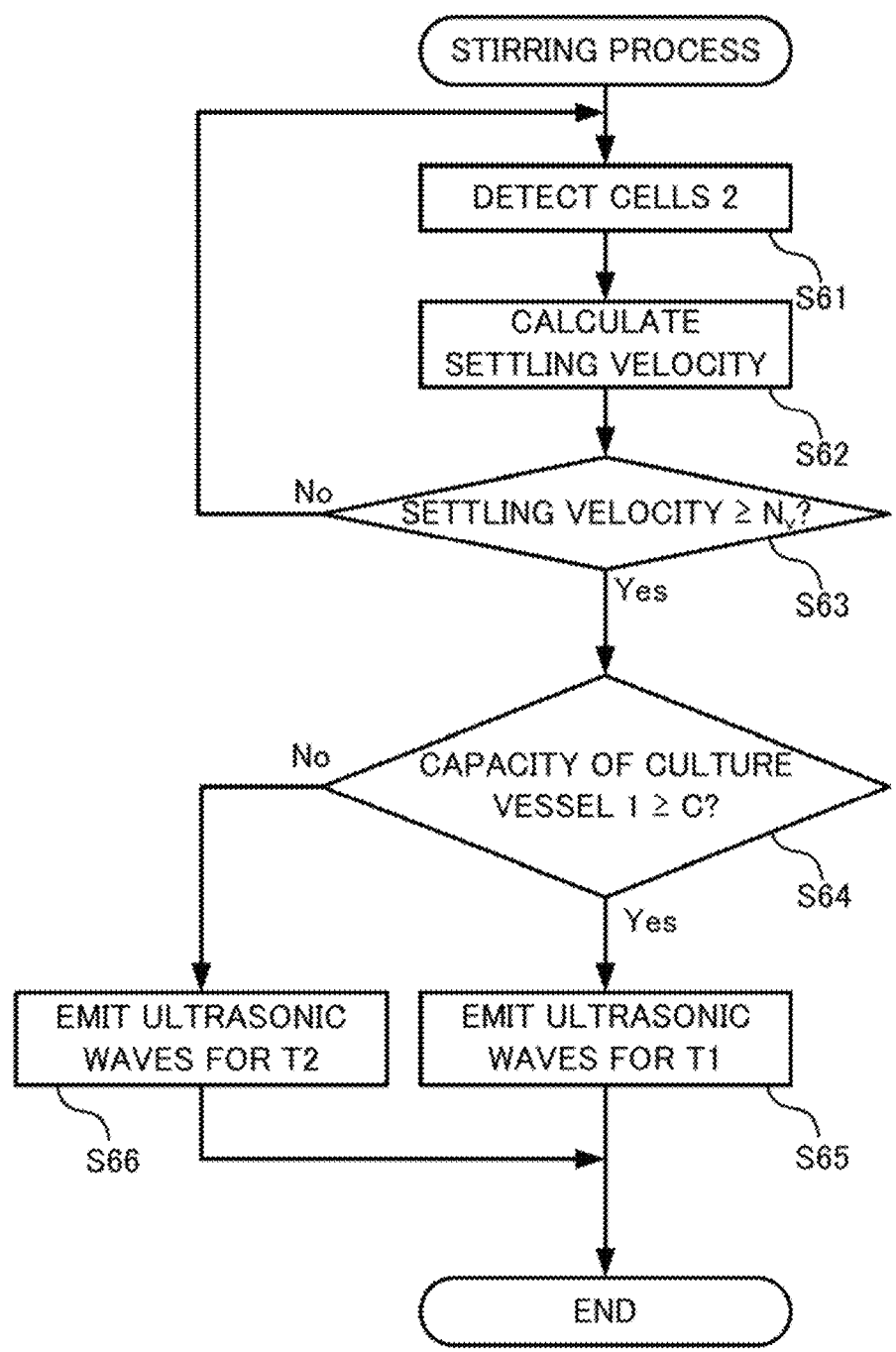
FIG. 23 is a flowchart of a stirring process performed by the cell culture device shown in FIG. 22.

A stirring process performed by the cell culture device 800 will now be described with reference to the flowchart shown in FIG. 23. Before the start of culturing, information about the culture vessel 1 is input through the vessel information setting unit 19 into the cell culture device 800. The acquirer 14 calculates the capacity of the culture vessel 1 based on the information about the culture vessel 1 and stores the capacity of the culture vessel 1 into the storage 111.

During culturing, the detector 13 detects cells 2 in the culture solution 3 (step S61). The acquirer 14 acquires a settling velocity based on positional information (step S62). The controller 15 determines whether the settling velocity of a cell 2 is higher than or equal to $N_v$ (step S63). When the settling velocity is higher than or equal to $N_v$ (Yes in step S63), the controller 15 refers to the storage 111 and determines whether the capacity of the culture vessel 1 is greater than or equal to C (step S64).

When the capacity of the culture vessel 1 is greater than or equal to C (Yes in step S64), the controller 15 emits ultrasonic waves toward the culture solution 3 for the duration T1 (step S65) and ends the stirring process. When the capacity of the culture vessel 1 is less than C (No in step S64), the controller 15 emits ultrasonic waves toward the culture solution 3 for the duration T2 (step S66) and ends the stirring process.

As described above, the cell culture device 800 according to the present embodiment adjusts the duration for irradiation of ultrasonic waves emitted to the culture solution 3 in accordance with the capacity of the culture vessel 1. When the culture vessel 1 has a large capacity, ultrasonic waves in an amount used to suspend cells 2 is emitted. When the culture vessel 1 has a smaller capacity, cells 2 can be suspended with ultrasonic irradiation in a possible minimum amount. This prevents excessive ultrasonic irradiation to the culture solution 3, while maintaining the condition of the culture solution 3 suitable for culturing cells 2.

The information about the culture vessel 1 may be a code for identifying a general-purpose culture vessel used for culturing cells. In this case, the acquirer 14 refers to a table associating a code prestored in the storage 111 with the capacity of a culture vessel identified by the code, and acquires the capacity of a culture vessel based on a code input by the user. The cell culture device 800 may additionally have functions described in other embodiments.

Embodiment 7

Figure 24:
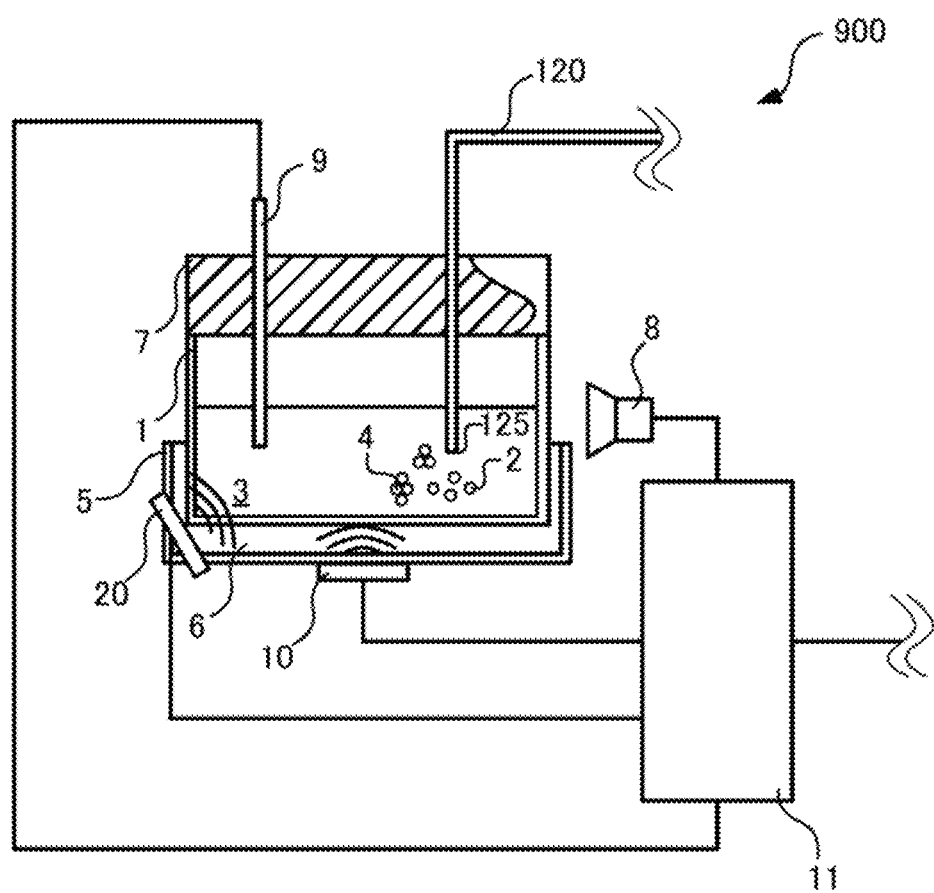
FIG. 24 is a schematic diagram of a cell culture device according to Embodiment 7 of the present disclosure.

A cell culture device 900 according to Embodiment 7 of the present disclosure will now be described focusing on the differences from the cell culture device 100 according to Embodiment 1 described above. As shown in FIG. 24, the cell culture device 900 further includes, in addition to the components of the cell culture device 100, a standing wave generator 20 that generates standing waves.

Standing waves are waves observed to have no propagation. A standing wave has a maximum amplitude at a location called an antinode and a minimum amplitude at a location called a node while vibrating repeatedly. Cells 2 can be held at nodes of standing waves generated in the culture solution 3.

The controller 15 controls the operation of the standing wave generator 20. The controller 15 generates nodes of standing waves at any position in the culture solution 3 by adjusting the wavelength, frequency, and amplitude of ultrasonic waves emitted from the standing wave generator 20. Nodes of standing waves generated near the inlet port 125 allow the cell collection unit 12 to collect cells 2 gathered at the nodes efficiently.

The operation of the cell culture device 900 will now be described. The controller 15 controls the operation of the transducer 10 based on information indicating the settling state of cells 2 to culture cells 2. After culturing, the controller 15 emits standing waves with the standing wave generator 20. The controller 15 waits until cells 2 stay at nodes of the standing waves.

The inlet port 125 is placed near the standing wave nodes at which cells 2 gather. The suction pump controller 122 drives the suction pump 121, causing cells 2 gathered at the standing wave nodes to be collected in the collection bag 123.

As described above, the cell culture device 900 according to the present embodiment can gather cells 2 at any position using standing waves. Thus, cells 2 can be collected efficiently by gathering cells 2 at the location of the inlet port 125. The cell culture device 900 may include a drive to move the inlet port 125 to any position in the culture vessel 1. The cell culture device 900 can collect cells 2 efficiently by moving, with the drive, the inlet port 125 to the position at which cells 2 are gathered by standing waves.

In the structure of the cell culture device 200, the transducers 10 and 10a may function as the standing wave generator 20 when the transducers 10 and 10a are arranged to emit the respective ultrasonic waves U1 and ultrasonic waves U2 traveling in opposite directions. In this case, when the ultrasonic waves U1 have the same wavelength, frequency, and amplitude as the ultrasonic waves U2, the ultrasonic waves U1 and U2 interfere with each other, thus being combined into standing waves.

A reflector placed to reflect ultrasonic waves emitted from the transducer 10 back to the transducer 10 may also function as the standing wave generator 20. Ultrasonic waves emitted from the transducer 10 and ultrasonic waves reflected by the reflector can generate standing waves.

In all the embodiments described above, the emitting direction of ultrasonic waves emitted from the transducer 10 or the transducer 10a may be changed manually or with an automatic positioner using, for example, a motor.

In the control of repeatedly driving and stopping the transducer 10 in all the embodiments described above, the controller 15 may change the ratio between the driving duration and the stopping duration based on information indicating the settling state of cells 2 and information indicating the size of a cell 2. For example, the controller 15 may set, for larger cells 2, a shorter stopping duration relative to the driving duration.

The control program 115 and various software programs used by the control unit 11 may be stored in a non-transitory computer-readable recording medium, such as a compact disc read-only memory (CD-ROM), a digital versatile disc (DVD), a magneto-optical disc, a universal serial bus (USB) memory, a memory card, and a hard disk drive (HDD), and may then be distributed. When the control program 115 and the various software programs are installed in a dedicated or general-purpose computer, the computer may then function as the control unit 11.

The control program 115 and the various software programs may be stored in a storage device in another server on the Internet and may then be downloaded from the server.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

REFERENCE SIGNS LIST

1 Culture vessel
2 Cell
3 Culture solution
4 Cell aggregate
5 Tank
6 Liquid
7 Lid
7a Cell culture flask
8 Optical sensor
9, 9a Culture solution sensor
10, 10a Transducer
11 Control unit
12 Cell collection unit
13 Detector
14 Acquirer
15 Controller
16 Output unit
17 Light source
18 Fluorescent substance
19 Vessel information setting unit
20 Standing wave generator
110 Ultrasonic transducer control circuit
111 Storage
112 RAM
113 CPU
114 Bus
115 Control program
120 Tube
121 Suction pump
122 Suction pump controller
123 Collection bag
124 Open-close valve
125 Inlet port
100, 200, 300, 400, 500, 600, 700, 800, 900 Cell culture device
p1, p2, p3, p4 Image

The invention claimed is:

1. A cell culture device, comprising:
an irradiator to emit ultrasonic waves toward a culture solution stored with cells in a culture vessel; and
processing circuitry to
  detect the cells in the culture solution,
  acquire information indicating a settling state of the detected cells, and
  cause the irradiator to emit the ultrasonic waves when the cells are in the settling state based on the information indicating the settling state of the cells,
wherein the information indicating the settling state of the cells includes a settling velocity calculated by dividing a settling distance determined from coordinates of a cell in two images captured at different times by an elapsed time between capture of the two images, and
the processing circuitry compares the settling velocity to a threshold velocity and, when the settling velocity is higher than or equal to the threshold velocity, causes the irradiator to emit the ultrasonic waves.

2. The cell culture device according to claim 1, wherein the information indicating the settling state includes a terminal velocity of the cells.

3. The cell culture device according to claim 1, wherein the processing circuitry
acquires information indicating a size of the detected cells, and
controls the operation of the irradiator based on the information indicating the size of the cells.

4. The cell culture device according to claim 1, wherein the information indicating the settling state of the cells includes information indicating a settling degree of the cells in the culture vessel acquired from distribution of the detected cells in the culture vessel.

5. The cell culture device according to claim 1, wherein the culture solution contains a first substance having the same distribution as the cells or cell aggregates of the cells in the culture solution,
the processing circuitry detects the first substance in the culture solution, and the information indicating the settling state of the cells includes information indicating a settling degree of the first substance in the culture vessel acquired from distribution of the detected first substance in the culture vessel.

6. The cell culture device according to claim 1, wherein the processing circuitry detects a second substance distributed in the culture solution in accordance with distribution of the cells or cell aggregates of the cells in the culture solution, and the information indicating the settling state of the cells includes information indicating distribution of the second substance in the culture solution.

7. The cell culture device according to claim 1, wherein the processing circuitry acquires information correlated with the number of the detected cells in the culture solution, and provides a notification to a user based on the information correlated with the number of the cells.

8. The cell culture device according to claim 1, wherein the processing circuitry detects a concentration of a third substance contained in the culture solution, and controls the operation of the irradiator based on the concentration of the third substance.

9. The cell culture device according to claim 1, wherein the cells are collected based on the information indicating the settling state of the cells.

10. The cell culture device according to claim 9, further comprising:

a standing wave generator to generate a standing wave, wherein the cells gathered by the standing wave are collected.

11. The cell culture device according to claim 1, wherein the processing circuitry acquires information indicating a change in the number of the detected cells contained in the culture solution detected, and the cells are collected based on the information indicating the change in the number of the cells.

12. The cell culture device according to claim 1, wherein the processing circuitry controls the operation of the irradiator based on information about a capacity of the culture vessel.

* * * * *